(12) United States Patent
Nakamura et al.

(10) Patent No.: US 10,596,191 B2
(45) Date of Patent: Mar. 24, 2020

(54) POLYMER CONJUGATE OF HEXA-COORDINATED PLATINUM COMPLEX

(71) Applicant: Nippon Kayaku Kabushiki Kaisha, Chiyoda-ku, Tokyo (JP)

(72) Inventors: Masaharu Nakamura, Tokyo (JP); Tsuyoshi Fukuda, Tokyo (JP); Yusaku Kikuchi, Tokyo (JP); Chihiro Watanabe, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/759,295

(22) PCT Filed: Sep. 8, 2016

(86) PCT No.: PCT/JP2016/076482
§ 371 (c)(1),
(2) Date: Mar. 12, 2018

(87) PCT Pub. No.: WO2017/047497
PCT Pub. Date: Mar. 23, 2017

(65) Prior Publication Data
US 2018/0250332 A1    Sep. 6, 2018

(30) Foreign Application Priority Data

Sep. 14, 2015   (JP) ................................ 2015-180875

(51) Int. Cl.
| | | |
|---|---|---|
| *A61K 33/24* | (2019.01) | |
| *A61K 47/10* | (2017.01) | |
| *A61K 47/34* | (2017.01) | |
| *A61P 35/00* | (2006.01) | |
| *C07F 15/00* | (2006.01) | |
| *C08G 65/333* | (2006.01) | |
| *C08G 65/337* | (2006.01) | |
| *C08G 69/10* | (2006.01) | |
| *C08G 69/40* | (2006.01) | |
| *C08G 69/48* | (2006.01) | |

(52) U.S. Cl.
CPC .............. *A61K 33/24* (2013.01); *A61K 47/10* (2013.01); *A61K 47/34* (2013.01); *A61P 35/00* (2018.01); *C07F 15/00* (2013.01); *C08G 65/333* (2013.01); *C08G 65/337* (2013.01); *C08G 69/10* (2013.01); *C08G 69/40* (2013.01); *C08G 69/48* (2013.01)

(58) Field of Classification Search
CPC ... C07F 15/0086–0093; C07F 15/0006; C08G 69/10

See application file for complete search history.

(56) References Cited

U.S. PATENT DOCUMENTS

| | | | |
|---|---|---|---|
| 4,431,666 A | 2/1984 | Bulten et al. | |
| 4,482,569 A | 11/1984 | Bulten et al. | |
| 4,658,048 A | 4/1987 | Totani et al. | |
| 4,845,124 A * | 7/1989 | Kidani ................ | C07F 15/0093 514/492 |
| 5,041,578 A | 8/1991 | Khokhar | |
| 5,072,011 A | 12/1991 | Abrams et al. | |
| 5,393,909 A | 2/1995 | Khokhar et al. | |
| 5,434,256 A | 7/1995 | Khokhar et al. | |
| 6,008,395 A | 12/1999 | Kidani | |
| 9,556,214 B2 | 1/2017 | Bilodeau et al. | |
| 2001/0038830 A1 | 11/2001 | Stewart et al. | |
| 2004/0097423 A1 | 5/2004 | Siddik et al. | |
| 2004/0175387 A1 | 9/2004 | Nowotnik et al. | |
| 2006/0067910 A1 | 3/2006 | Kitagawa et al. | |
| 2006/0222696 A1 | 10/2006 | Okada et al. | |
| 2007/0148125 A1 | 6/2007 | Kataoka et al. | |
| 2007/0197427 A1 | 8/2007 | Nowotnik et al. | |
| 2011/0081404 A1 | 4/2011 | Okada et al. | |
| 2011/0110881 A1 | 5/2011 | Kataoka et al. | |

(Continued)

FOREIGN PATENT DOCUMENTS

| | | |
|---|---|---|
| EP | 0237450 A2 | 9/1987 |
| EP | 1536864 A2 | 6/2005 |

(Continued)

OTHER PUBLICATIONS

International Search Report and Written Opinion dated Sep. 20, 2016 in co-pending PCT application No. PCT/JP2016/067903.
Liu et al., "Oxidative Addition of CI2, HClO to Square-Planar PtII Complexes: Synthesis and Structural Characterization of Platinum(II) and Platinum(IV) Bis(amidate) Complexes", European Journal of Inorganic Chemistry, 2006, pp. 1168-1173.
Misset et al., "Oxaliplatin Clinical Activity: A Review", Critical Reviews in Oncology/Hematology, vol. 35, 2000, pp. 75-93.
Ravera et al., "A New Entry to Asymmetric Platinum (IV) Complexes via Oxidative Chlorination", Inorganic Chemistry, 53, 2014, pp. 9326-9335.
Wilson et al., "Synthetic Methods for the Preparation of Platinum Anticancer Complexes", Chemical Reviews, 114, 2014, pp. 4470-4495.

(Continued)

*Primary Examiner* — Amanda L Aguirre
(74) *Attorney, Agent, or Firm* — Nields, Lemack & Frame, LLC

(57) ABSTRACT

A DDS preparation of a platinum complex, which selectively releases a highly active platinum complex in cells that are under reducing conditions, and exhibits high antitumor activity that is required from a medicine, is still not available, and there is a demand for a novel DDS preparation of a platinum complex that may be used in clinical fields. There is provided a polymer conjugate of a hexa-coordinated platinum complex, the polymer conjugate comprising a block copolymer having a polyethylene glycol structural moiety and a polyaspartic acid moiety or a polyglutamic acid moiety; and a hexa-coordinated platinum complex having a halogen atom and a hydroxyl group at the axial positions, the hexa-coordinated platinum complex being bonded, directly or via a spacer, to a side-chain carboxyl group of the block copolymer.

12 Claims, No Drawings

(56) References Cited

U.S. PATENT DOCUMENTS

| | | | | |
|---|---|---|---|---|
| 2014/0288244 A1* | 9/2014 | Yamamoto | ........... | C08G 65/333 525/434 |
| 2014/0363491 A1 | 12/2014 | Okada et al. | | |
| 2018/0179239 A1 | 6/2018 | Nakamura et al. | | |

FOREIGN PATENT DOCUMENTS

| | | | | | |
|---|---|---|---|---|---|
| EP | 1695991 | A1 | | 8/2006 | |
| EP | 2305275 | A1 | | 4/2011 | |
| FR | 2954321 | A1 | | 6/2011 | |
| JP | 61-7283 | A | | 1/1986 | |
| JP | 62-207283 | A | | 9/1987 | |
| JP | 1-294684 | A | | 11/1989 | |
| JP | 3-279392 | A | | 12/1991 | |
| JP | 5-117385 | A | | 5/1993 | |
| JP | 3268913 | B2 | | 3/2002 | |
| JP | 2006-504691 | A | | 2/2006 | |
| JP | 3955992 | B2 | | 8/2007 | |
| JP | 2008-538105 | A | | 10/2008 | |
| JP | 2011-105792 | A | | 6/2011 | |
| JP | 2011105792 | A | * | 6/2011 | ................ C07J 9/00 |
| JP | 2011-137046 | A | | 7/2011 | |
| JP | 4745664 | B2 | | 8/2011 | |
| JP | 5458255 | B2 | | 4/2014 | |
| SU | 1186617 | A1 | | 10/1985 | |
| WO | 90/005734 | A1 | | 5/1990 | |
| WO | 96/026949 | A1 | | 9/1996 | |
| WO | 2004/024062 | A2 | | 3/2004 | |
| WO | 2005/056641 | A1 | | 6/2005 | |
| WO | 2011/058776 | A1 | | 5/2011 | |
| WO | 2014/100417 | A1 | | 6/2014 | |

OTHER PUBLICATIONS

Office action dated Sep. 19, 2018 in co-pending U.S. Appl. No. 15/579,754.
Jehn et al., "Pharmacokinetics of Liposomal Cisplatin (Lipoplatin) in Combination with 5-FU in Patients with Advanced Head and Neck Cancer: First Results of a Phase III Study", Anticancer Research, vol. 27, pp. 471-475, 2007.
Shanmugam et al., "Oligonucleotides—Assembled Au Nanorod-Assisted Cancer Photothermal Ablation and Combination Chemotherapy with Targeted Dual-Drug Delivery of Doxorubicin and Cisplatin Prodrug", ACS Applied Materials & Interfaces, vol. 6, pp. 4382-4393, 2014.
Wang et al., "Co-Delivery of Oxaliplatin and Demethylcantharidin via a Polymer-Drug Conjugate", Macromolecular Bioscience, vol. 14, pp. 588-596, 2014.
Hou et al., "A Core Cross-Linked Polymeric Micellar Platinum(IV) Prodrug with Enhanced Anticancer Efficiency", Macromolecular Bioscience, vol. 13, pp. 954-965, 2013.
Scarano et al., "Folate Conjugation to Polymeric Micelles via Boronic Acid Ester to Deliver Platinum Drugs to Ovarian Cancer Cell Lines", Biomacromolecules, vol. 14, pp. 962-975, 2013.

Du et al., "Nanoparticle delivery of photosensitive Pt(IV) drugs for circumventing cisplatin cellular pathway and on-demand drug release", Colloids and Surfaces B: Biointerfaces, vol. 123, pp. 734-741, 2014.
Xiao et al., "Co-delivery of daunomycin and oxaliplatin by biodegradable polymers for safer and more efficacious ,combination therapy", Journal of Controlled Release, vol. 163, pp. 304-314, 2012.
Xiao et al., "A prodrug strategy to deliver cisplatin(IV) and paclitaxel in nanomicelles to improve efficacy and tolerance", Biomaterials, vol. 33, pp. 6507-6519, 2012.
Graf et al., "Platinum(IV)-chlorotoxin (CTX) conjugates for targeting cancer cells", Journal of Inorganic Biochemistry, vol. 110, pp. 58-63, 2012.
Hall et al., "Basis for Design and Development of Platinum(IV) Anticancer Complexes", Journal of Medical Chemistry, vol. 50, No. 15, pp. 3403-3411, Jul. 26, 2007.
Zheng et al., "Pt(IV) Prodrugs Designed to Bind Non-Covalently to Human Serum Albumin for Drug Delivery", Journal of the American Chemical Society, vol. 136, pp. 8790-8798, 2014.
Xiao et al., "Biodegradable polymer cisplatin(IV) conjugate as a pro-drug of cisplatin(II)", Biomaterials, vol. 32, pp. 7732-7739, 2011.
International Search Report and Written Opinion dated Nov. 22, 2016 in corresponding PCT application No. PCT/JP2016/076482.
Final rejection dated Apr. 30, 2019 in co-pending U.S. Appl. No. 15/579,754.
Xu et al., "Mono- and Di-Bromo Platinum(IV) Prodrugs via Oxidative Bromination: Synthesis, Characterization, and Cytotoxicity," Dalton Transactions, vol. 44, No. 46, pp. 19918-19926, 2015.
European communication dated Feb. 12, 2019 in co-pending European patent application No. 16814252.9.
Russian communication, with English translation, dated Mar. 29, 2019 in co-pending Russian patent application No. 2017140223/04.
European communication dated Mar. 28, 2019 in corresponding European patent application No. 16846368.5.
Office action dated Sep. 11, 2019 in co-pending U.S. Appl. No. 15/579,754.
Office action dated Sep. 17, 2019 in co-pending U.S. Appl. No. 16/431,811.
Chinese communication, with English translation, dated Sep. 16, 2019 in co-pending Chinese patent application No. 201680035654. 5.
Taiwanese communication, with English translation, dated Oct. 5, 2019 in co-pending Taiwanese patent application No. 105119624.
Indian communication dated Oct. 25, 2019 in co-pending Indian patent application No. 201817000967.
Wexselblatt et al., "Platinum (IV) Prodrugs with Haloacetato Ligands in the Axial Positions can Undergo Hydrolysis Under Biologically Relevant Conditions", Angewandte Chemie, vol. 52, Iss. 23, pp. 6059-6062, May 2013.
European communication dated Nov. 22, 2019 in co-pending European patent application No. 16814252.9.

* cited by examiner

POLYMER CONJUGATE OF HEXA-COORDINATED PLATINUM COMPLEX

TECHNICAL FIELD

The present invention relates to a polymer conjugate of a hexa-coordinated platinum complex having antitumor activity, and a medicine comprising the polymer conjugate as an active ingredient.

BACKGROUND ART

Platinum complexes such as cisplatin and oxaliplatin are used in various cancerous regions as key drugs for multidrug therapy in cancer chemotherapy. However, it is known that the platinum complexes cause kidney disorders, nausea and vomiting, peripheral nerve disorders, bone marrow suppression, and the like as side effects, and this has been a problem for clinical use.

For the purpose of reducing these side effects and enhancing therapeutic effects, development of platinum complexes utilizing drug delivery technologies is in progress. Examples of DDS preparations of platinum complexes that have hitherto progressed to clinical trial stages may include, but not limited to, a coordination compound of platinum(II) diaminocyclohexane with a block copolymer (NC-4016) (see Patent Document 1), targeted liposomes (MBP-426) having oxaliplatin encapsulated therein (see Patent Document 2), a N,O-amidomalonate platinum diamine complex (AP5346) (see Patent Document 3), a coordination compound of cisplatin with a block copolymer (see Patent Document 4), and a liposome preparation of cisplatin (Lipoplatin) (see non-Patent Document 1). However, DDS preparations of platinum complexes that have come to be available in the market still do not exist.

In the above-mentioned DDS preparations of platinum complexes that have progressed to clinical trial stages, tetra-coordinated platinum complexes are used as the platinum complex; however, DDS preparations using hexa-coordinated platinum complexes have also been reported. Specific examples of a DDS preparation using a hexa-coordinated platinum complex may include a compound comprising gold nanorods as a carrier (see Non Patent Document 2), a compound obtained by conjugating a serine/threonine phosphatase-2A inhibitor between a carrier and a hexa-coordinated platinum complex (see Non Patent Document 3), a compound obtained by crosslinking a polymer as a carrier using a hexa-coordinated platinum complex (see Non Patent Document 4), a compound obtained by modifying micelles that include a hexa-coordinated platinum complex with folic acid (see Non Patent Document 5), a compound having a photoresponsive hexa-coordinated platinum complex conjugated to a carrier (see Non Patent Document 6), a compound capable of forming micelles by conjugating a hexa-coordinated platinum complex and daunomycin respectively to a polymer (see Non Patent Document 7), a compound capable of forming micelles by conjugating a hexa-coordinated platinum complex and paclitaxel respectively to a polymer (see Non Patent Document 8), and a compound having a cancer-targeting peptide conjugated to a hexa-coordinated platinum complex (see Non Patent Document 9).

An advantage of using a hexa-coordinated platinum complex may be that the hexa-coordinated platinum complex can be conjugated to a carrier of a DDS by a method different from that using a tetra-coordinated platinum complex, by utilizing the ligands at the axial positions. Furthermore, it is said that a hexa-coordinated platinum complex is generally less active compared to a tetra-coordinated platinum complex and is reduced to a tetra-coordinated complex by a substance having reducing activity in cells to thereby exhibit antitumor activity. Thus, it is expected that side effects will be reduced by using a hexa-coordinated complex (see Non Patent Document 10). Examples of a compound having reducing activity in cells may include glutathione and ascorbic acid, and it is known that the concentrations of those compounds in cells (including cancer cells) are higher than the concentrations of the compounds in blood. Thus, it is considered that a hexa-coordinated platinum complex is selectively converted to a highly active tetra-coordinated platinum complex in an reducing environment in cells. Meanwhile, although the values may vary depending on the Document, the intracellular concentration of ascorbic acid is 300 to 10,000 μM, and the concentration in blood is 30 to 51 μM (see Non Patent Documents 4 and 11). Releasability of a platinum complex from a carrier under the conditions with adding ascorbic acid has been demonstrated in Non Patent Documents 4 and 7.

In regard to the reducing property of low-molecular weight hexa-coordinated platinum complexes, it is known that the reducing property varies with the ligands at the axial positions. However, all of the hexa-coordinated platinum complexes used in Non Patent Documents 2 to 9 mentioned above are compounds in which any one or both of hydroxyl groups of a hexa-coordinated platinum complex which has two hydroxyl groups as ligands at the axial positions, are bonded to a carrier by ester bonding, and no further development has been progressed.

PRIOR ART DOCUMENTS

Patent Documents

Patent Documents 1: JP 3955992 B2
Patent Documents 2: JP 2008-538105 W
Patent Documents 3: JP 2011-137046 A
Patent Documents 4: JP 5458255 B2

Non Patent Documents

Non Patent Documents 1: ANTICANCER RESEARCH, 2007, 27, 471-476
Non Patent Documents 2: ACS Appl. Mater. Interfaces, 2014, 6, 4382-4393
Non Patent Documents 3: Macromol. Biosci., 2014, 14, 588-596
Non Patent Documents 4: Macromol. Biosci., 2013, 13, 954-965
Non Patent Documents 5: Biomacromolecules, 2013, 14, 962-975
Non Patent Documents 6: Colloids and Surfaces B: Biointerfaces, 2014, 123, 734-741
Non Patent Documents 7: Journal of Controlled Release, 2012, 163, 304-314
Non Patent Documents 8: Biomaterials, 2012, 33, 6507-6519
Non Patent Documents 9: Journal of Inorganic Biochemistry, 2012, 110, 58-63
Non Patent Documents 10: J. Med. Chem., 2007, 50, 3403-3411
Non Patent Documents 11: J. Am. Chem. Soc., 2014, 136, 8790-8798

SUMMARY OF INVENTION

Problem to be Solved

A DDS preparation of a platinum complex that selectively releases a highly active platinum complex in cells, which are under reducing conditions as described above, and exhibits high antitumor activity that is required as a medicine, still cannot be obtained, and a novel DDS preparation of a platinum complex that may be used in clinical fields is desired. That is, regarding the DDS preparations that use hexa-coordinated platinum complexes including the compounds described above, since there is no compound that is clinically used as in the case of DDS preparations of tetra-coordinated platinum complexes, there is a demand for a clinically useful DDS preparation of a hexa-coordinated platinum complex, which releases a highly active tetra-coordinated platinum complex under the reducing conditions in cells by means of a particular hexa-coordinated platinum complex and a DDS carrier.

Solution to Problem

The inventors of the present invention conducted studies thoroughly in order to solve the problems described above, and as a result, the inventors found that a polymer derivative of a hexa-coordinated platinum complex obtainable by ester-bonding, directly or via a linker, a hexa-coordinated platinum complex having a halogen atom and a hydroxyl group at the axial positions to a side-chain carboxyl group in a block copolymer having a polyethylene glycol structural moiety and a polyaspartic acid moiety or a polyglutamic acid moiety, efficiently releases the platinum complex under reducing conditions in cells and exhibits antitumor activity. Thus, the inventors completed the present invention.

That is, the present invention relates to the following (1) to (16).

(1) A polymer conjugate of a hexa-coordinated platinum complex, the polymer conjugate comprising a block copolymer having a polyethylene glycol structural moiety and a polyaspartic acid moiety or a polyglutamic acid moiety; and a hexa-coordinated platinum complex having a halogen atom and a hydroxyl group at the axial positions, the hexa-coordinated platinum complex being bonded, directly or via a spacer, to a side-chain carboxyl group of the block copolymer.

(2) The polymer conjugate of a hexa-coordinated platinum complex according to (1), wherein the polymer conjugate is represented by the following Formula (I):

wherein $R_1$ represents a hydrogen atom, a (C1-C10) alkyl group which may have a substituent, or a (C6-C10) aryl group; $R_2$ represents a bonding group; $R_3$ represents a hydrogen atom or a (C1-C6) acyl group; $R_4$ represents a residue of a hexa-coordinated platinum complex having a halogen atom and a hydroxyl group at the axial positions, or a substituent selected from the group represented by the following Formula (II):

[Chemical Formula 2] (II)

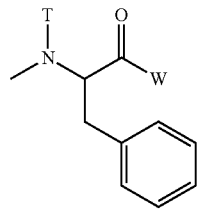

(i)

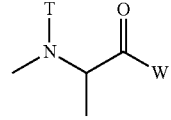

(ii)

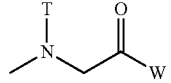

(iii)

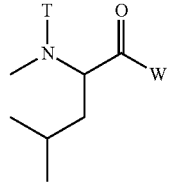

(iv)

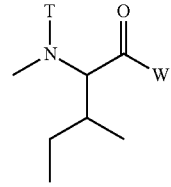

(v)

[Chemical Formula 1]

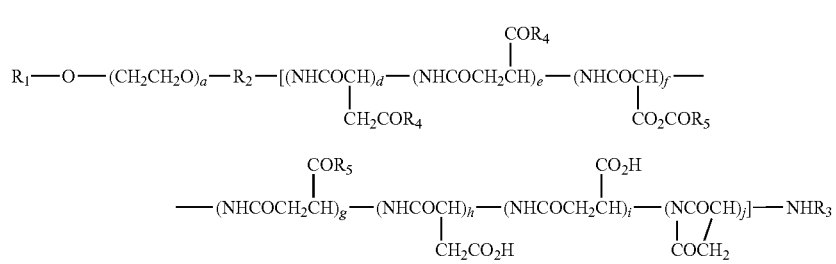

(I)

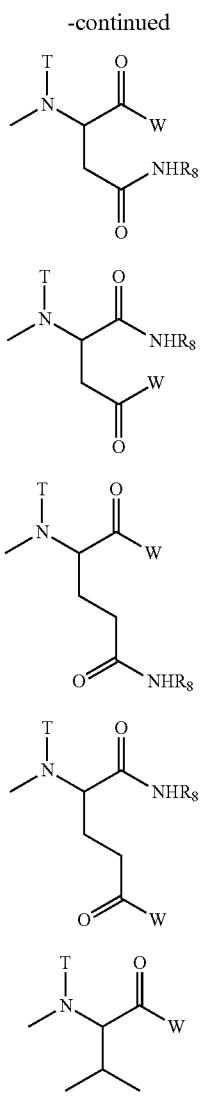

(vi)

(vii)

(viii)

(ix)

(x)

[wherein W represents a substituent selected from the group consisting of a residue of a hexa-coordinated platinum complex having a halogen atom and a hydroxyl group at the axial positions, a hydroxyl group, an amino group having a benzyl group or a (C1-C10) alkyl group which may have a substituent, a (C1-C10) alkoxy group which may have a phenyl group, a (C6-C10) aryloxy group, and —NR$_6$CONHR$_7$; R$_6$ and R$_7$ may be identical or different, and each represents a (C3-C6) cyclic alkyl group, or a (C1-C5) alkyl group which may be substituted with a tertiary amino group; T represents a hydrogen atom, a (C1-C10) alkyl group which may have a substituent, or a (C6-C10) aryl group; and R$_8$ represents a (C1-C10) alkyl group which may have a substituent, a benzyl group, or a residue of an amino acid having the carboxylic acid protected], provided that at least one W among the substituents represents a residue of a hexa-coordinated platinum complex having a halogen atom and a hydroxyl group at the axial positions; R$_5$ represents a substituent selected from the group consisting of a (C1-C30) alkoxy group, a (C1-C30) aralkyloxy group, a (C6-C10) aryloxy group, a (C1-C30) alkylamino group which may have a substituent, a di(C1-C30) alkylamino group which may have a substituent, a substituent represented by the following Formula (III) obtained by eliminating H from an α-amino group of an α-amino acid derivative:

[Chemical Formula 3]

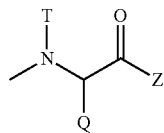

(III)

[wherein Q represents a side chain residue of an α-amino acid; T represents a hydrogen atom, a (C1-C10) alkyl group which may have a substituent, or a (C6-C10) aryl group; Z represents a substituent selected from the group consisting of an amino group having a benzyl group or a (C1-C10) alkyl group which may have a substituent, a (C1-C10) alkoxy group which may have a phenyl group, a (C6-C10) aryloxy group, and —NR$_{12}$CONHR$_{13}$; and R$_2$ and R$_{13}$ may be identical or different, and each represents a (C3-C6) cyclic alkyl group, or a (C1-C5) alkyl group which may be substituted with a tertiary amino group], and —NR$_9$CONHR$_{10}$; R$_9$ and R$_{10}$ may be identical or different, and each represents a (C3-C6) cyclic alkyl group, or a (C1-C5) alkyl group which may be substituted with a tertiary amino group; a represents an integer from 5 to 11,500; d, e, f, g, h, i, and j each represents an integer from 0 to 200; d+e represents an integer from 1 to 200; d+e+f+g+h+i+j represents an integer from 2 to 200; and the bonding order of the various constituent units of the polyaspartic acid is arbitrary.

(3) The polymer conjugate of a hexa-coordinated platinum complex according to (2), wherein R$_1$ represents a (C1-C3) alkyl group which may have a substituent; R$_2$ represents a (C2-C6) alkylene group; R$_3$ represents a (C1-C3) acyl group; R$_4$ represents a residue of a hexa-coordinated platinum complex having a halogen atom and a hydroxyl group at the axial positions, or a substituent selected from the group consisting of the following Formula (IV):

[Chemical Formula 4]

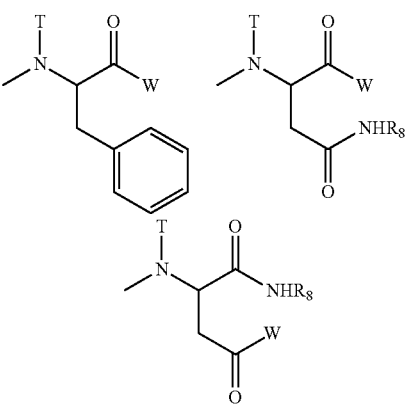

(IV)

[wherein W, T, and R$_8$ mean the same groups as W, T, and R$_8$ of Formula (II), respectively], provided that at least one W among the substituents represents a residue of a hexa-coordinated platinum complex having a halogen atom and a hydroxyl group at the axial positions; a represents an integer from 10 to 2,000; d, e, f, g, h, i, and j each represents an integer from 0 to 100; d+e represents an integer from 1 to 100; and d+e+f+g+h+i+j represents an integer from 4 to 100.

(4) The polymer conjugate of a hexa-coordinated platinum complex according to (2) or (3), wherein $R_1$ represents a methyl group; $R_2$ represents a trimethylene group; $R_3$ represents an acetyl group; $R_4$ represents a residue of a hexa-coordinated platinum complex having a halogen atom and a hydroxyl group at the axial positions; $R_5$ represents a substituent selected from the group consisting of a residue obtained by eliminating H from an amino group of phenylalanine benzyl ester, and $-NR_9CONHR_{10}$; and $R_9$ and $R_{10}$ both represent a cyclohexyl group or an isopropyl group.

(5) The polymer conjugate of a hexa-coordinated platinum complex according to (2) or (3), wherein $R_1$ represents a methyl group; $R_2$ represents a trimethylene group; $R_3$ represents an acetyl group; $R_4$ represents a substituent selected from the group represented by the following Formula (V):

[Chemical Formula 5]

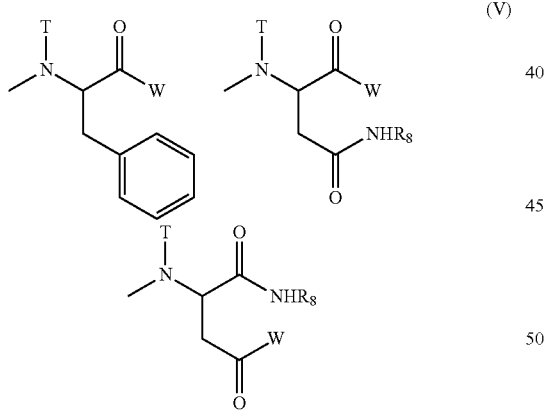

(V)

[wherein W represents a substituent selected from the group consisting of a residue of a hexa-coordinated platinum complex having a halogen atom and a hydroxyl group at the axial positions, and $-NR_6CONHR_7$; $R_6$ and $R_7$ both represent a cyclohexyl group or an isopropyl group; T represents a hydrogen atom, a methyl group, an ethyl group, or a benzyl group; and $R_8$ represents a residue of an amino acid having the carboxylic acid protected], provided that at least one W among the substituents represents a residue of a hexa-coordinated platinum complex having a halogen atom and a hydroxyl group at the axial positions; $R_5$ represents $-NR_9CONHR_{10}$; and $R_9$ and $R_{10}$ both represent a cyclohexyl group or an isopropyl group.

(6) The polymer conjugate of a hexa-coordinated platinum complex according to (1), wherein the polymer conjugate is represented by the following Formula (VI):

[Chemical Formula 6]

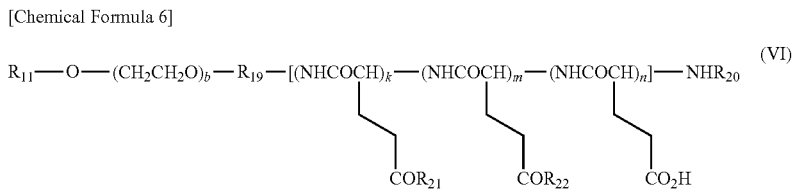

(VI)

wherein $R_{11}$ represents a hydrogen atom, a (C1-C10) alkyl group which may have a substituent, or a (C6-C10) aryl group; $R_{19}$ represents a bonding group; $R_{20}$ represents a hydrogen atom or a (C1-C6) acyl group; $R_{21}$ represents a residue of a hexa-coordinated platinum complex having a halogen atom and a hydroxyl group at the axial positions, or a substituent selected from the group represented by the following Formula (VII):

[Chemical Formula 7] (VII)

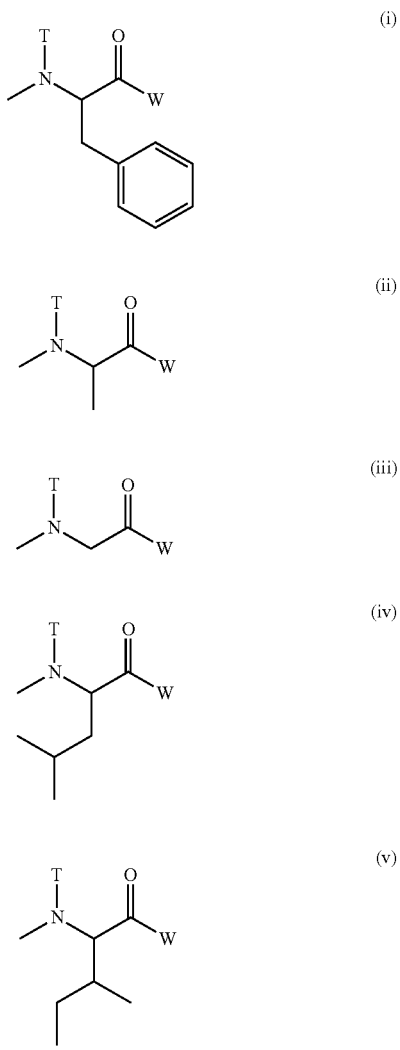

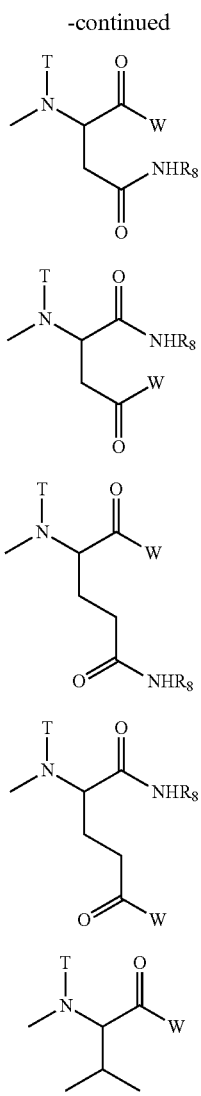

(vi)

(vii)

(viii)

(ix)

(x)

[wherein W represents a substituent selected from the group consisting of a residue of a hexa-coordinated platinum complex having a halogen atom and a hydroxyl group at the axial positions, a hydroxyl group, an amino group having a benzyl group or a (C1-C10) alkyl group which may have a substituent, a (C1-C10) alkoxy group which may have a phenyl group, a (C6-C10) aryloxy group, and —$NR_{16}CONHR_{17}$; $R_{16}$ and $R_{17}$ may be identical or different, and each represents a (C3-C6) cyclic alkyl group, or a (C1-C5) alkyl group which may be substituted with a tertiary amino group; T represents a hydrogen atom, a (C1-C10) alkyl group which may have a substituent, or a (C6-C10) aryl group; $R_8$ represents a (C1-C10) alkyl group which may have a substituent, a benzyl group, or a residue of an α-amino acid having the carboxylic acid protected], provided that at least one W among the substituents represents a residue of a hexa-coordinated platinum complex having a halogen atom and a hydroxyl group at the axial positions; $R_{22}$ represents a substituent selected from the group consisting of a (C1-C30) alkoxy group, a (C1-C30) aralkyloxy group, a (C6-C10) aryloxy group, a (C1-C30) alkylamino group which may have a substituent, a di(C1-C30) alkylamino group which may have a substituent, a residue represented by the following Formula (VIII) obtained by eliminating H from an α-amino group of an α-amino acid derivative:

[Chemical Formula 8]

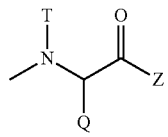

(VIII)

[wherein Q represents a side chain residue of an α-amino acid; T represents a hydrogen atom, a (C1-C10) alkyl group which may have a substituent, or a (C6-C10) aryl group; Z represents a substituent selected from the group consisting of an amino group having a benzyl group or a (C1-C10) alkyl group which may have a substituent, a (C1-C10) alkoxy group which may have a phenyl group, a (C6-C10) aryloxy group, and —$NR_{24}CONHR_{25}$; $R_{24}$ and $R_{25}$ may be identical or different, and each represents a (C3-C6) cyclic alkyl group, or a (C1-C5) alkyl group which may be substituted with a tertiary amino group], and —$NR_{14}CONHR_{15}$; $R_{14}$ and $R_{15}$ may be identical or different, and each represents a (C3-C6) cyclic alkyl group, or a (C1-C5) alkyl group which may be substituted with a tertiary amino group; b represents an integer from 5 to 11,500; k represents an integer from 1 to 200; m and n each represents an integer from 0 to 200; k+m+n represents an integer from 2 to 200; and the bonding order of the various constituent units of the polyglutamic acid is arbitrary.

(7) The polymer conjugate of a hexa-coordinated platinum complex according to (6), wherein $R_{11}$ represents a (C1-C3) alkyl group which may have a substituent; $R_{19}$ represents a (C2-C6) alkylene group; $R_{20}$ represents a (C1-C3) acyl group; $R_{21}$ represents a residue of a hexa-coordinated complex having a halogen atom and a hydroxyl group at the axial positions, or a substituent selected from the group consisting of the following Formula (IX):

[Chemical Formula 9]

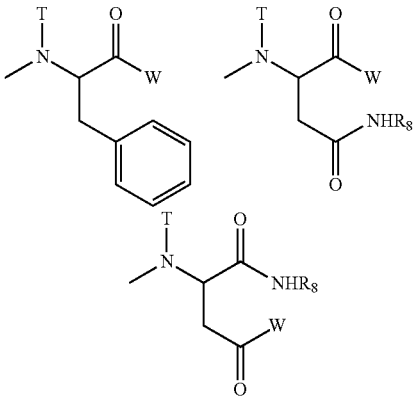

(IX)

[wherein W, T, and $R_8$ mean the same groups as W, T, and $R_8$ of Formula (VII), respectively], provided that at least one W among the substituents represents a residue of a hexa-coordinated platinum complex having a halogen atom and a hydroxyl group at the axial positions; b represents an integer from 10 to 2,000; k represents an integer from 1 to 100; m and n each represents an integer from 0 to 100; and k+m+n represents an integer from 3 to 100.

(8) The polymer conjugate of a hexa-coordinated platinum complex according to (6) or (7), wherein $R_{11}$ represents a methyl group; $R_{19}$ represents a trimethylene group; $R_{20}$ represents an acetyl group; $R_{21}$ represents a residue of a hexa-coordinated platinum complex having a halogen atom and a hydroxyl group at the axial positions; $R_{22}$ represents a substituent selected from the group consisting of a residue obtained by eliminating H from an amino group of phenylalanine benzyl ester, and —$NR_{14}CONHR_{15}$; and $R_{14}$ and $R_{15}$ both represent a cyclohexyl group or an isopropyl group.

(9) The polymer conjugate of a hexa-coordinated platinum complex according to (6) or (7), wherein $R_{11}$ represents a methyl group; $R_{19}$ represents a trimethylene group; $R_{20}$ represents an acetyl group; $R_{21}$ represents a substituent selected from the group represented by the following Formula (X):

[Chemical Formula 10]

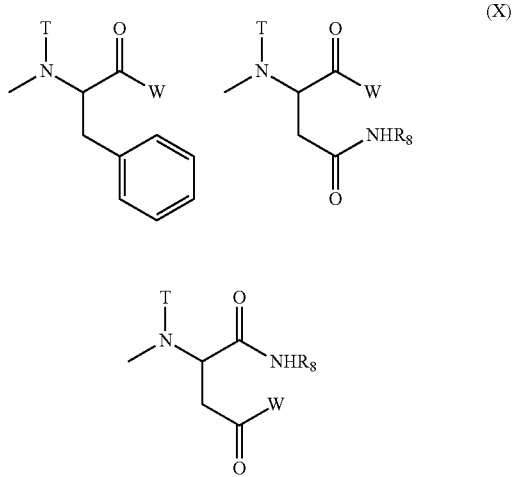

(X)

[wherein W represents a substituent selected from the group consisting of a residue of a hexa-coordinated platinum complex having a halogen atom and a hydroxyl group at the axial positions, and —$NR_{16}CONHR_{17}$; $R_{16}$ and $R_{17}$ both represent a cyclohexyl group or an isopropyl group; T represents a hydrogen atom, a methyl group, an ethyl group, or a benzyl group; and $R_8$ represents a residue of an amino acid having the carboxylic acid protected], provided that at least one W among the substituents represents a residue of a hexa-coordinated platinum complex having a halogen atom and a hydroxyl group at the axial positions; $R_{22}$ represents —$NR_{14}CONHR_{15}$; and $R_{14}$ and $R_{15}$ both represent a cyclohexyl group or an isopropyl group.

(10) The polymer conjugate of a hexa-coordinated platinum complex according to any one of (1) to (9), wherein the hexa-coordinated platinum complex having a halogen atom and a hydroxyl group at the axial positions is a hexa-coordinated platinum complex represented by the following Formula (XI):

[Chemical Formula 11]

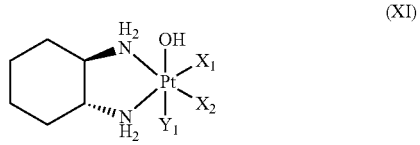

(XI)

wherein $X_1$ and $X_2$ both represent a halogen atom, or the two are linked together to form a dicarboxylate selected from the group consisting of oxalate, malonate, succinate, and o-phthalate; and $Y_1$ represents a halogen atom.

(11) The polymer conjugate of a hexa-coordinated platinum complex according to (10), wherein $Y_1$ of the hexa-coordinated platinum complex represents a chlorine atom or a bromine atom; $X_1$ and $X_2$ both represent a chlorine atom or a bromine atom, or the two are linked together to form oxalate.

(12) A method for producing the polymer conjugate of a hexa-coordinated platinum complex according to (1), wherein a carboxyl group in a side chain of the block copolymer having a polyethylene glycol structural moiety and a polyaspartic acid moiety or a polyglutamic acid moiety, and a hydroxyl group of the hexa-coordinated platinum complex having a halogen atom and a hydroxyl group at the axial positions are ester-bonded using a dehydration condensation agent.

(13) A method for producing the polymer conjugate of a hexa-coordinated platinum complex according to (1), wherein a linker to which the hydroxyl group of the hexa-coordinated platinum complex having a halogen atom and a hydroxyl group at the axial positions is ester-bonded, is bonded to a carboxyl group in a side chain of the block copolymer having a polyethylene glycol structural moiety and a polyaspartic acid moiety or a polyglutamic acid moiety.

(14) A method for producing the polymer conjugate of a hexa-coordinated platinum complex according to (1), wherein a linker bonded to a carboxyl group in a side chain of the block copolymer having a polyethylene glycol structural moiety and a polyaspartic acid moiety or a polyglutamic acid moiety, and the hydroxyl group of the hexa-coordinated platinum complex having a halogen atom and a hydroxyl group at the axial positions are ester-bonded.

(15) A medicine comprising the polymer conjugate of a hexa-coordinated platinum complex according to any one of (1) to (11) as an active ingredient.

(16) An antitumor agent comprising the polymer conjugate of a hexa-coordinated platinum complex according to any one of (1) to (11) as an active ingredient.

Effects of Invention

The present polymer conjugate of a hexa-coordinated platinum complex having a halogen atom and a hydroxyl group at the axial positions efficiently releases the platinum complex under reducing conditions in cancer cells, and a medicine containing the polymer conjugate as an active ingredient functions as a drug which exhibits effective antitumor activity with less side effects such as peripheral nerve disorders in clinical treatment.

DESCRIPTION OF EMBODIMENTS

Details of the present invention will be described below.
The present polymer conjugate of a hexa-coordinated platinum complex is such that a hexa-coordinated platinum complex having a halogen atom and a hydroxyl group at the axial positions is ester-bonded, directly or via a spacer, to a side-chain carboxyl group in a block copolymer having a polyethylene glycol structural moiety and a polyaspartic acid moiety or a block copolymer having a polyethylene glycol structural moiety and a polyglutamic acid moiety.

The polyethylene glycol structural moiety according to the present invention includes a polyethylene glycol having two modified ends or a single modified end, and the modifying groups at the two ends may be identical or different. Examples of the terminal modifying group may include a methyl group, an ethyl group, a n-propyl group, an isopropyl group, a n-butyl group, a s-butyl group, a t-butyl group, a benzyl group, a 4-phenylbutyl group, a dimethoxyethyl group, a diethoxyethyl group, an aminoethyl group, an aminopropyl group, and an aminobutyl group. Among them, preferred examples may include a (C1-C3) alkyl group which may have a substituent, an aminoethyl group, and an aminopropyl group.

The molecular weight of the polyethylene glycol structural moiety is usually about 200 to 500,000, preferably about 300 to 100,000, and more preferably about 1,000 to 50,000.

The number of bonds of the polyaspartic acid moiety or polyglutamic acid moiety of the block copolymer is, on the average, 1 to 300 bonds, preferably 2 to 200 bonds, and more preferably 3 to 100 bonds, per molecule. The number of bonds may be determined by neutralization titration of the raw material block copolymer by means of alkali.

The hexa-coordinated platinum complex having a halogen atom and a hydroxyl group at the axial positions according to the present invention is not particularly limited as long as the central metal atom is platinum (IV), and the ligands at the axial positions are a halogen atom and a hydroxyl group.

The present polymer conjugate of the hexa-coordinated platinum complex is a compound in which this hydroxyl group is ester-bonded to a side-chain carboxyl group in a block copolymer having a polyethylene glycol structural moiety and a polyaspartic acid moiety or a polyethylene glycol structural moiety and a polyglutamic acid moiety, or a carboxyl group of a linker that is bonded to that carboxyl group.

The polyaspartic acid moiety according to the present invention may be a polymer of α-form or β-form, or may be a polymer in which the α-form and the β-form are mixed, and preferably, the polyaspartic acid moiety is a polymer in which the α-form and the β-form are mixed.

The polyglutamic acid moiety according to the present invention may be a polymer of α-form or γ-form, or may be a polymer in which the α-form and the γ-form are mixed, and preferably, the polyglutamic acid moiety is a polymer of α-form.

The polyaspartic acid moiety or polyglutamic acid moiety according to the present invention may comprise D-amino acids only or L-amino acids only, or it is also acceptable that D-amino acids and L-amino acids exist in an arbitrary mixture.

In regard to the present block copolymer, the bonding amount of the polymer conjugate of the hexa-coordinated platinum complex and the block copolymer having a polyethylene glycol structural moiety and a polyaspartic acid moiety or a polyglutamic acid moiety is not particularly limited as long as the bonding amount is an amount that exhibits efficacy. However, usually, the bonding amount is 1% to 100%, and preferably 5% to 80%, of the total number of carboxyl groups of the polymer.

The halogen atom according to the present invention means a fluorine atom, a chlorine atom, a bromine atom, or an iodine atom.

The (C1-C10) alkyl group which may have a substituent according to the present invention is a linear, branched, or cyclic (C1-C10) alkyl group, and examples may include a methyl group, an ethyl group, a n-propyl group, a n-butyl group, a n-pentyl group, a n-hexyl group, a n-octyl group, a n-decyl group, an isopropyl group, a s-butyl group, a t-butyl group, a 2,2-dimethylpropyl group, a cyclopropyl group, a cyclobutyl group, a cyclopentyl group, a cyclohexyl group, an adamantly group, a benzyl group, a phenethyl group, a 4-phenylbutyl group, a dimethoxyethyl group, a diethoxyethyl group, a dimethoxypropyl group, a diethoxypropyl group, an aminoethyl group, a diaminoethyl group, an aminopropyl group, and an aminobutyl group.

Examples of the (C6-C10) aryl group according to the present invention may include a phenyl group and a naphthyl group.

The present polymer conjugate of a hexa-coordinated platinum complex, in which a side-chain carboxyl group in a block copolymer having a polyethylene glycol structural moiety and a polyaspartic acid moiety is bonded, directly or via a spacer, to a hexa-coordinated platinum complex having a halogen atom and a hydroxyl group at the axial positions, is represented by, for example, Formula (I) shown above.

Examples of the (C1-C10) alkyl group which may have a substituent for $R_1$ of Formula (I) may include the substituents exemplified above, and among them, a (C1-C3) alkyl group which may have a substituent is preferred, while a methyl group is particularly preferred.

Examples of the (C6-C10) aryl group for $R_1$ of Formula (I) may include the substituents mentioned above as examples.

The bonding group represented by $R_2$ of Formula (I) may be, for example, a linear or branched (C2-C6) alkylene group. Above all, a linear (C2-C4) alkylene group is preferred, and examples may include an ethylene group, a trimethylene group, and a tetramethylene group, while a trimethylene group is particularly preferred.

Examples of the (C1-C6) acyl group for $R_3$ of Formula (I) may include a formyl group, an acetyl group, a propionyl group, and a pivaloyl group, and a (C1-C3) acyl group is preferred, while an acetyl group is particularly preferred.

$R_4$ of Formula (I) is a residue of the hexa-coordinated platinum complex having a halogen atom and a hydroxyl group at the axial positions as mentioned above, or a substituent of Formula (II).

The residue of the hexa-coordinated platinum complex having a halogen atom and a hydroxyl group at the axial positions is a group obtained by eliminating H from the hydroxyl group of the hexa-coordinated platinum complex mentioned above.

Examples of the (C1-C10) alkyl group which may have a substituent for W of Formula (II) may include the substituents mentioned above as examples, and among them, an ethyl group and a t-butyl group are preferred.

Examples of the (C1-C10) alkoxy group which may have a phenyl group for W of Formula (II) may include a methoxy group, an ethoxy group, a n-propoxy group, an isopropoxy group, a t-butoxy group, a benzyloxy group, a phenethyloxy group, and a 4-phenyl-1-butoxy group.

Examples of the (C6-C10) aryloxy group for W of Formula (II) may include a phenoxy group and a naphthoxy group.

Examples of the (C3-C6) cyclic alkyl group for $R_6$ and $R_7$ of —$NR_6CONHR_7$ of W of Formula (II) may include a cyclopropyl group, a cyclobutyl group, a cyclopentyl group, and a cyclohexyl group, and among them, a cyclohexyl group is preferred. Furthermore, examples of the (C1-C5) alkyl group which may be substituted with a tertiary amino group may include a methyl group, an ethyl group, a n-propyl group, a n-butyl group, a n-pentyl group, an isopropyl group, a dimethylaminopropyl group, and a 2-morpholinoethyl group, and among them, an isopropyl group and a dimethylaminopropyl group are preferred.

Examples of the (C1-C10) alkyl group which may have a substituent for T of Formula (II) may include the substituents mentioned above as examples, and preferred examples may include a methyl group, an ethyl group, a n-propyl group, and a benzyl group.

Examples of the (C6-C10) aryl group for T of Formula (II) may include the substituents mentioned above as examples.

Particularly preferred examples for T of Formula (II) may include a hydrogen atom, a methyl group, an ethyl group, and a benzyl group.

Examples of the (C1-C10) alkyl group which may have a substituent for $R_8$ of Formula (II) may include the substituents mentioned above as examples, and among them, an ethyl group, a phenyl group, a benzyl group, and a 4-phenyl-1-butyl group are preferred. The amino acid residue having a protected carboxyl group is not particularly limited; however, preferred examples may include (C1-C3) alkyl esters, unsubstituted amides, dimethylamides, diethylamides, and dibenzylamides of glycine, alanine, leucine, isoleucine, valine, and phenylalanine.

The substituent represented by Formula (II) for $R_4$ of Formula (I) is preferably a substituent represented by Formula (IV) [wherein W, T, and $R_8$ mean the same groups as W, T, and $R_8$ of Formula (II), respectively], and a substituent represented by Formula (V) [wherein W represents a substituent selected from the group consisting of a residue of a hexa-coordinated platinum complex having a halogen atom and a hydroxyl group at the axial positions, and —$NR_6CONHR_7$; $R_6$ and $R_7$ both represent a cyclohexyl group or an isopropyl group; T represents a hydrogen atom, a methyl group, an ethyl group, or a benzyl group; and $R_8$ represents a residue of an amino acid having its carboxylic acid protected] is particularly preferred.

$R_5$ of Formula (I) represents a group selected from the group consisting of a (C1-C30) alkoxy group, a (C1-C30) aralkyloxy group, a (C6-C10) aryloxy group, a (C1-C30) alkylamino group which may have a substituent, a di(C1-C30) alkylamino group which may have a substituent, an α-amino acid derivative represented by Formula (III) [wherein Q represents a side chain residue of an α-amino acid; T represents a hydrogen atom, a (C1-C10) alkyl group which may have a substituent, or a (C6-C10) aryl group; Z represents a substituent selected from the group consisting of an amino group having a benzyl group or a (C1-C10) alkyl group which may have a substituent, a (C1-C10) alkoxy group which may have a phenyl group, a (C6-C10) aryloxy group, and —$NR_{12}CONHR_{13}$; and $R_{12}$ and $R_{13}$ may be identical or different, and each represents a (C3-C6) cyclic alkyl group, or a (C1-C5) alkyl group which may be substituted with a tertiary amino group], and —$NR_9CONHR_{10}$, while $R_9$ and $R_{10}$ may be identical or different, and each represents a (C3-C6) cyclic alkyl group, or a (C1-C5) alkyl group which may be substituted with a tertiary amino group.

Examples of the (C1-C30) alkoxy group may include a methoxy group, an ethoxy group, a n-butoxy group, a t-butoxy group, a cyclopropoxy group, a cyclohexyloxy group, and an adamantyloxy group, and among them, an ethoxy group and a t-butoxy group are preferred.

Examples of the (C1-C30) aralkyloxy group may include a benzyloxy group, a 2-phenylethoxy group, a 3-phenylpropoxy group, and a 4-phenylbutoxy group, and among them, a benzyloxy group and a 4-phenyl-1-butoxy group are preferred.

Examples of the (C6-C10) aryloxy group may include a phenoxy group and a naphthoxy group.

Examples of the (C1-C30) alkylamino group which may have a substituent and a di(C1-C30) alkylamino group which may have a substituent may include a methylamino group, an ethylamino group, a butylamino group, an isopropylamino group, a cyclohexylamino group, a benzylamino group, a 4-phenylbutylamino group, a dimethylamino group, a diethylamino group, a dibutylamino group, a diisopropylamino group, a dicyclohexylamino group, a dibenzylamino group, a diphenylbutylamino group, a N-ethylmethylamino group, a N-methylphenylamino group, and a N-methyl-4-phenylbutylamino group, and among them, an ethylamino group, a benzylamino group, and a 4-phenylbutylamino group are preferred.

Q of the α-amino acid derivative represented by Formula (III) is preferably a side chain of an essential amino acid, and examples thereof may include a hydrogen atom, a methyl group, a benzyl group, and an isobutyl group. A benzyl group, which is a side chain of phenylalanine, is particularly preferred. Furthermore, examples of the (C1-C10) alkyl group which may have a substituent in Z may include the substituents mentioned above as examples, and among them, a methyl group, an ethyl group, a phenyl group, a benzyl group, and a 4-phenyl-1-butyl group are preferred.

Examples of the (C1-C10) alkyl group which may have a substituent and the (C6-C10) aryl group for T may include the same groups as those mentioned for T of Formula (II), and preferred groups are also similar.

Examples of the (C1-C10) alkoxy group which may have a phenyl group for Z may include a methoxy group, an ethoxy group, a n-propoxy group, an isopropoxy group, a t-butoxy group, a benzyloxy group, a phenethyloxy group, and a 4-phenylbutoxy group.

Examples of the (C6-C10) aryloxy group for Z may include a phenoxy group and a naphthoxy group.

In a case in which Z represents —$NR_{12}CONHR_{13}$, examples of the (C3-C6) cyclic alkyl group and the (C1-C5) alkyl group which may be substituted with a tertiary amino group for $R_{12}$ and $R_{13}$ may include the same groups as those mentioned above for $R_6$ and $R_7$ of W of Formula (II), and preferred groups are also similar.

Among them, a benzyloxy group is particularly preferable as Z.

Examples of the (C3-C6) cyclic alkyl group and the (C1-C5) alkyl group which may be substituted with a tertiary amino group for $R_9$ and $R_{10}$ of —$NR_9CONHR_{10}$ for $R_5$ of Formula (I) may include the same groups as those mentioned above for $R_6$ and $R_7$ of W of Formula (II), and preferred groups are also similar.

The substituents of $R_5$ of Formula (I) in one molecule may be identical or different, and a single substituent may be used, or a mixture of substituents may be used, among molecules of the polymer conjugate of a hexa-coordinated platinum complex.

Particularly preferred examples of the substituent for $R_5$ of Formula (I) may include residues obtained by eliminating H from the amino groups of phenylalanine benzyl ester, N-methylphenylalanine benzyl ester, N-ethylphenylalanine benzyl ester, and N-benzylphenylalanine benzyl ester; and —NR$_9$CONHR$_{10}$ mentioned above.

a of Formula (I) represents an integer from 5 to 11,500, and a is preferably 10 to 2,000.

d, e, f, g, h, i, and j of Formula (I) each represents an integer from 0 to 200, and d+e represents an integer from 1 to 200, while d+e+f+g+h+i+j represents an integer from 2 to 200. Preferably, d, e, f, g, h, i, and j each represents an integer from 0 to 100, d+e represent an integer from 1 to 100, f+g represents an integer from 0 to 99, h+i represents an integer from 0 to 30, and d+e+f+g+h+i+j represents an integer from 4 to 100.

In regard to the polymer conjugate of a hexa-coordinated platinum complex represented by Formula (I), the bonding order of the various constituents of polyaspartic acid is arbitrary.

The polymer conjugate of a hexa-coordinated platinum complex of the present invention, in which a hexa-coordinated platinum complex having a halogen atom and a hydroxyl group at the axial positions is bonded, directly or via a spacer, to a side-chain carboxyl group in a block copolymer having a polyethylene glycol structural moiety and a polyglutamic acid moiety, is represented by, for example, Formula (VI) described above.

Examples of the (C1-C10) alkyl group which may have a substituent for R$_{11}$ of Formula (VI) may include the substituents mentioned above as examples, and among them, a (C1-C3) alkyl group which may have a substituent is preferred, while a methyl group is particularly preferred.

Examples of the (C6-C10) aryl group for R$_{11}$ of Formula (VI) may include the substituents mentioned above as examples.

Examples of the bonding group represented by R$_{19}$ of Formula (VI) may include the same groups as the bonding groups for R$_2$ of Formula (I), and preferred groups are also similar.

Examples of the (C1-C6) acyl group for R$_{20}$ of Formula (VI) may include the same groups as the (C1-C6) acyl group for R$_3$ of Formula (I), and preferred groups are also similar.

R$_{21}$ of Formula (VI) represents a residue of a hexa-coordinated platinum complex having a halogen atom and a hydroxyl group at the axial positions, or a substituent of Formula (VII), as described above.

The residue of a hexa-coordinated platinum complex having a halogen atom and a hydroxyl group at the axial positions is a group obtained by eliminating H from the hydroxyl group of the hexa-coordinated platinum complex mentioned above.

Examples of the (C1-C10) alkyl group which may have a substituent, (C1-C10) alkoxy group which may have a phenyl group, and (C6-C10) aryloxy group for W of Formula (VII), and examples of the (C3-C6) cyclic alkyl group and the (C1-C5) alkyl group which may be substituted with a tertiary amino group for R$_{16}$ and R$_{17}$ of —NR$_{16}$CONHR$_{17}$ may include the same groups as the (C1-C10) alkyl group which may have a substituent, (C1-C10) alkoxy group which may have a phenyl group, and (C6-C10) aryloxy group for W of Formula (II), and the (C3-C6) cyclic alkyl group and the (C1-C5) alkyl group which may be substituted with a tertiary amino group for R$_6$ and R$_7$ of —NR$_6$CONHR$_7$, respectively. Preferred groups are also similar.

Examples of the (C1-C10) alkyl group which may have a substituent for T of Formula (VII) may include the substituents mentioned above as examples, and preferred examples may include a methyl group, an ethyl group, a n-propyl group, and a benzyl group.

Examples of the (C6-C10) aryl group for T of Formula (VII) may include the substituents mentioned above as examples.

Particularly preferred examples of T of Formula (VII) may include a hydrogen atom, a methyl group, an ethyl group, and a benzyl group.

Examples of the (C1-C10) alkyl group which may have a substituent and the amino acid residue having a protected carboxyl group for R$_8$ of Formula (VII) may include the same groups as the (C1-C10) alkyl group which may have a substituent and the amino acid residue having a protected carboxyl group for R$_8$ of Formula (II), and preferred groups are also similar.

The substituent represented by Formula (VII) for R$_{21}$ of Formula (VI) is preferably a substituent represented by Formula (IX) [wherein W, T, and R$_9$ mean the same groups as W, T, and R$_8$ of Formula (VII), respectively], and a substituent represented by Formula (X) [wherein W represents a substituent selected from the group consisting of a residue of a hexa-coordinated platinum complex having a halogen atom and a hydroxyl group at the axial positions, and —NR$_{16}$CONHR$_{17}$; R$_{16}$ and R$_{17}$ both represent a cyclohexyl group or an isopropyl group; T represents a hydrogen atom, a methyl group, an ethyl group, or a benzyl group; and R$_8$ represents a residue of an amino acid having its carboxylic acid protected] is particularly preferred.

R$_{22}$ of Formula (VI) represents a group selected from the group consisting of a (C1-C30) alkoxy group, a (C1-C30) aralkyloxy group, a (C6-C10) aryloxy group, a (C1-C30) alkylamino group which may have a substituent, a di(C1-C30) alkylamino group which may have a substituent, an α-amino acid derivative represented by Formula (VIII): [wherein Q represents a side chain residue of an α-amino acid; T represents a hydrogen atom, a (C1-C10) alkyl group which may have a substituent, or a (C6-C10) aryl group; Z represents a substituent selected from the group consisting of an amino group having a benzyl group or a (C1-C10) alkyl group which may have a substituent, a (C1-C10) alkoxy group which may have a phenyl group, a (C6-C10) aryloxy group, and —NR$_{24}$CONHR$_{25}$; and R$_{24}$ and R$_{25}$ may be identical or different, and each represents a (C3-C6) cyclic alkyl group, or a (C1-C5) alkyl group which may be substituted with a tertiary amino group], and —NR$_{14}$CONHR$_{15}$. R$_{14}$ and R$_{15}$ may be identical or different, and each represents a (C3-C6) cyclic alkyl group, or a (C1-C5) alkyl group which may be substituted with a tertiary amino group.

Here, examples of the (C1-C30) alkoxy group, (C1-C30) aralkyloxy group, (C6-C10) aryloxy group, (C1-C30) alkylamino group which may have a substituent, and di(C1-C30) alkylamino group which may have a substituent, may include the same groups as the (C1-C30) alkoxy group, (C1-C30) aralkyloxy group, (C6-C10) aryloxy group, (C1-C30) alkylamino group which may have a substituent, and di(C1-C30) alkylamino group which may have a substituent for R$_5$ of Formula (I), respectively, and preferred groups are also similar.

Examples of Q and T of the α-amino acid derivative represented by Formula (VIII) may include the same groups as Q and T of the α-amino acid derivative represented by Formula (III), and preferred groups are also similar. Furthermore, examples of the (C1-C10) alkyl group which may have a substituent, (C1-C10) alkoxy group which may have a phenyl group, and a (C6-C10) aryloxy group for Z of Formula (VIII), and the (C3-C6) cyclic alkyl group and the (C1-C5) alkyl group which may be substituted with a tertiary amino group for R$_{24}$ and R$_{25}$ of —NR$_{24}$CONHR$_{25}$, may include the same groups as the (C1-C10) alkyl group which may have a substituent, (C1-C10) alkoxy group which may have a phenyl group, and (C6-C10) aryloxy group for Z of Formula (III), and the (C3-C6) cyclic alkyl group and the (C1-C5) alkyl group which may be substituted with a tertiary amino group for $R_{12}$ and $R_{13}$ of —$NR_{12}CONHR_{13}$ mentioned above, respectively, and preferred groups are also similar.

Among them, a benzyloxy group is particularly preferred as Z.

Examples of the (C3-C6) cyclic alkyl group and the (C1-C5) alkyl group which may be substituted with a tertiary amino group for $R_{14}$ and $R_{15}$ of —$NR_{14}CONHR_{15}$ for $R_{22}$ of Formula (VI) may include the same groups as those mentioned above for $R_6$ and $R_7$ of —$NR_6CONHR_7$ of W of Formula (II), and preferred groups are also similar.

The substituents of $R_{22}$ of Formula (VI) in one molecule may be identical or different, and a single substituent may be used, or a mixture of substituents may be used, among molecules of the polymer conjugate of a hexa-coordinated platinum complex.

Particularly preferred examples of the substituent of $R_{22}$ of Formula (VI) include residues obtained by eliminating H from an amino group of phenylalanine benzyl ester, N-methylphenylalanine benzyl ester, N-ethylphenylalanine benzyl ester, and N-benzylphenylalanine benzyl ester; and —$NR_{14}CONHR_{15}$ described above.

b of Formula (VI) represents an integer from 5 to 11,500, and an integer from 10 to 2,000 is preferred.

k of Formula (VI) represents an integer from 1 to 200, m and n each represents an integer from 0 to 200, and k+m+n represents an integer from 2 to 200. Preferably, k represents an integer from 1 to 100, m and n each represents an integer from 0 to 100, and k+m+n is 3 to 100. More preferably, m is 0 to 99, and n is 0 to 30.

In regard to the polymer conjugate of a hexa-coordinated platinum complex represented by Formula (VI), the bonding order of the various constituent units of polyglutamic acid is arbitrary.

Regarding the hexa-coordinated platinum complex having a halogen atom and a hydroxyl group at the axial positions according to the present invention, preferably, a hexa-coordinated platinum complex represented by Formula (XI) [wherein $X_1$ and $X_2$ both represent a halogen atom, or are linked together to form a dicarboxylate selected from the group consisting of oxalate, malonate, succinate, and o-phthalate; and $Y_1$ represents a halogen atom] may be used.

It is preferable that $X_1$ and $X_2$ of Formula (XI) both represent a chlorine atom or a bromine atom, or are linked together to form a dicarboxylate, and $Y_1$ is preferably a chlorine atom or a bromine atom.

The dicarboxylate is not particularly limited; however, a group in which two carboxyl groups are directly bonded, a (C1-C6) alkyl group having two carboxyl groups, or a (C6-C10) aryl group having two carboxyl groups at the ortho-positions is particularly preferred, and examples thereof may include oxalate (i), malonate (ii), succinate (iii), and o-phthalate (iv) shown below.

[Chemical Formula 12]

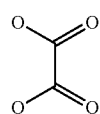

(i)

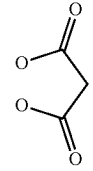

(ii)

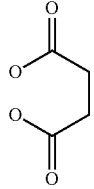

(iii)

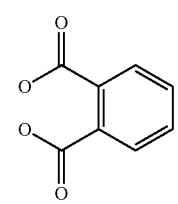

(iv)

The steric structure of the cyclohexane-1,2-diamine ligand that is preferably used for the present hexa-coordinated platinum complex is preferably trans-configuration of 1R and 2R.

Regarding the present hexa-coordinated platinum complex having a halogen atom and a hydroxyl group at the axial positions, compounds represented by the following Formulae (XII) and (XIII) are especially preferred.

[Chemical Formula 13]

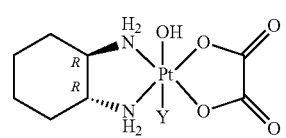

(XII)

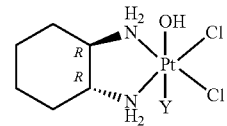

(XIII)

wherein $Y_1$ represents a chlorine atom or a bromine atom.

The polymer conjugate of a hexa-coordinated platinum complex represented by Formula (I) or (VI) may form a micelle in water, in which the polyethylene glycol structural moiety forms the outer shell, and the platinum complex conjugate moiety forms the inner shell. In that case, the particle size of the micelle is about 3 to 100 nm as measured by a particle size/zeta potential analyzer (Malvern Instruments Ltd; Zetasizer Nano ZS).

The hexa-coordinated platinum complex used in the present invention may be produced by applying the method described in Document such as Non Patent Document 10. That is, a method of obtaining a hexa-coordinated platinum complex by subjecting a tetra-coordinated platinum complex to an oxidizing agent treatment with hydrogen peroxide or the like or to an oxidative halogenations treatment, in a solvent; or a method of obtaining an intended a hexa-coordinated platinum complex by subjecting a hexa-coordinated platinum complex to a substitution reaction or a condensation reaction, is employed. An example of the production method will be described in the following Reference Example.

The present polymer conjugate of a hexa-coordinated platinum complex is obtained by ester-bonding a side-chain carboxyl group of a block copolymer having a polyethylene glycol structural moiety and a polyaspartic acid moiety or a polyglutamic acid moiety to a hydroxyl group of a hexa-coordinated platinum complex having a halogen atom and a hydroxyl group at the axial positions, which is obtainable by the production method described above, using a dehydration condensation agent or the like in an organic solvent, and the present production method is also included in the present invention. That is, for example, a production method of subjecting a block copolymer of a polyethylene glycol structural moiety and a polyaspartic acid moiety, which is produced by referring to the method described in JP 3268913 B, and a hexa-coordinated platinum complex having a halogen atom and a hydroxyl group at the axial positions, in which any functional groups other than the group to be reacted are protected as necessary, to a dehydration condensation reaction by means of dicyclohexylcarbodiimide (DCC), diisopropylcarbodiimide (DIPC), 1-ethyl-3-(3-dimethylaminopropyl)carbodiimide hydrochloride (WSC), 1-ethoxycarbonyl-2-ethoxy-1,2-dihydroxyquinolinone (EEDQ), (benzotriazole-1-yloxy)tripyrrolidinophosphonium hexafluorophosphate (PyBOP), N,N,N',N'-tetramethyl-O-(7-azabenzotriazol-1-yl)uranium hexafluorophosphate (HATU), or the like, in a solvent, preferably in an aprotic polar solvent such as N,N-dimethylformamide (DMF), 1,3-dimethyl-2-imidazolidinone (DMI), or N-methylpyrrolidone (NMP), at 0° C. to 180° C., and preferably at 5° C. to 50° C. Furthermore, at the time of the condensation reaction, an auxiliary reaction agent such as N,N-dimethylaminopyridine (DMAP), 1-hydroxybenzotriazole hydrate (HOBt.H$_2$O), or ethyl (hydroxyimino)cyanoacetate may also be used. After the condensation reaction, deprotection is performed as necessary, and as a result of the operation of conventional separation, purification and the like, a polymer conjugate of a hexa-coordinated platinum complex is produced. The present polymer conjugate of a hexa-coordinated platinum complex is similarly produced using a block copolymer of a polyethylene glycol structural moiety-polyglutamic acid moiety, by referring to the method described in JP 4745664 B.

Regarding the method of introducing a structure represented by Formula (II) or (VII) into $R_4$ or $R_{21}$ in the compound of Formula (I) or (VI), for example, the compound may be produced by amide-bonding a side-chain carboxyl group of a block copolymer having a polyethylene glycol structural moiety and a polyaspartic acid moiety or a polyglutamic acid moiety, to an amino acid derivative having its carboxylic acid protected or a N-monoalkyl form of the amino acid derivative using a dehydration condensation agent, performing deprotection of the carboxylic acid, and then introducing a substituent represented by W of Formula (II) or (VII) using a dehydration condensation agent.

Regarding the method for introducing a desired substituent into $R_5$ or $R_{22}$ in the compound of Formula (I) or (VI), a method of activating a carboxyl group of the block copolymer by means of a method of using conventional ester synthesis or amide synthesis, and then reacting a corresponding alcohol, a corresponding amine, or an amino acid derivative having a protected carboxyl group with the activated carboxyl group in an amount that is wished to form bonds under basic conditions; a method of activating a corresponding alcohol, a corresponding amine, an amino acid derivative having a protected carboxyl group, or the like, and then reacting the activating the resultant with a carboxyl group of the block copolymer; and the like may be used. After the product is purified, unreacted carboxyl groups in the polymer may be reactivated by a similar reaction, and a hydroxyl group of a hexa-coordinated platinum complex having a halogen atom and a hydroxyl group at the axial position may be condensed to the reactivated carboxyl groups. Alternatively, other alcohols, amines, and the like may be repeatedly reacted with the reactivated carboxyl groups to thereby synthesize a hybrid of various substituents of $R_5$ or $R_{22}$, and then the hydroxyl group of a hexa-coordinated platinum complex having a halogen atom and a hydroxyl group at the axial positions may be condensed with the hybrid. Furthermore, the reaction order of these processes may be different. The method for producing the present polymer conjugate of a hexa-coordinated platinum complex is not limited to these methods. Examples of the production method will also be described in the following Examples.

A medicine containing the present polymer conjugate of a hexa-coordinated platinum complex as an active ingredient is also included in the present invention. The use application is not particularly limited as long as the use application is a medicine application in which the present polymer conjugate of a hexa-coordinated platinum complex exhibits efficacy; however, a use application as an antitumor agent is preferred. The polymer conjugate as an antitumor agent may be used alone or after being mixed with pharmaceutically acceptable additives such as a preparation carrier, an excipient, a disintegrant, a binder, a lubricating agent, a fluidizing agent, a coating agent, a suspending agent, an emulsifier, a stabilizer, a preservative, a corrigent, a flavoring agent, a diluents, and a dissolution aid, and the medicine may be administered orally or parenterally (systemic administration, topical administration, or the like) in the form of preparations such as a powdered preparation, a granular preparation, a tablet, a caplet, a capsule, an injectable preparation, a suppository, and an ointment. Use as an injectable preparation is particularly preferred, and usually, for example, water, physiological saline, a 5% glucose or mannitol solution, a water-soluble organic solvent (for example, glycerol, ethanol, dimethyl sulfoxide, N-methylpyrrolidone, polyethylene glycol, CREMOPHOR, or a mixed liquid thereof), or a mixed liquid of water and the water-soluble organic solvent is used.

The amount of administration of the present polymer conjugate of a hexa-coordinated platinum complex may be definitely varied depending on the gender, age, and physiological status of the patient, the disease state, and the like; however, the present polymer conjugate of a hexa-coordinated platinum complex is usually administered parenterally in an amount of 0.01 to 1,500 mg/m$^2$, and preferably 0.1 to 250 mg/m$^2$, as an active ingredient per day for an adult. Administration by injection is carried out via veins, arteries, diseased areas (tumor areas), or the like.

EXAMPLES

Hereinafter, the present invention will be described in more detail by way of Examples. However, the present invention is not intended to be limited to these Examples.

In the Examples of the invention, the following abbreviations are used.

ox: oxalate
R,R-dach: (1R,2R)-cyclohexanediamine
l-OHP: oxaliplatin

The drug content of a compound in the present Examples was determined by quantitatively determining the platinum content using an inductively coupled plasma emission spectroscopic analyzer, ICP-OES (Agilent Technologies, Inc.; 720-ES type), and calculating the drug content from the platinum content.

The particle size and zeta potential of a compound in the present Examples were carried out using a particle size/zeta potential analyzer (Malvern Instruments Ltd: Zetasizer Nano ZS).

Measurement of the purity of a low molecular weight compound in the present Reference Example was carried out using high performance liquid chromatography, and using L-column2 ODS (4.6 mm I.D.×250 mm: purchased from Chemicals Evaluation and Research Institute, Japan) as a column; a buffer solution prepared by dissolving 2.72 g of potassium dihydrogen phosphate, 1.89 g of sodium 1-pentanesulfonate, and 0.5 ml of triethylamine in 2,000 ml of distilled water, and adjusting the solution to pH 4.3 with phosphoric acid, as mobile phase (A); and methanol as mobile phase (B), under the following analysis conditions 1 or 2.

Analysis conditions 1 (isocratic analysis):
Mobile phase (B) concentration: 15% (0 min) to 15% (20 min)
Mobile phase flow rate: 1 ml/min, detection: 210 nm.
Analysis conditions 2 (gradient analysis):
Mobile phase (B) concentration: 15% (0 min) to 90% (10 min)
Mobile phase flow rate: 1 ml/min, detection: 210 nm.

The molecular weight of a low molecular weight compound in the present Reference Example was measured using LC/MS (Shimadzu LCMS-2020), and using Inertsil ODS-3 (2.1 mm I.D.×100 mm) as a column; acetonitrile/formic acid (99.9/0.1) as mobile phase (A); and water/formic acid (99.9/0.1) as mobile phase (B), under the following analysis conditions 3 or 4.

Analysis Conditions 3

| Gradient | | | | | |
| --- | --- | --- | --- | --- | --- |
| Time (minutes) | 0.0 | 5.5 | 6.5 | 6.51 | 10.0 |
| Mobile phase (A) concentration (%) | 20 | 90 | 90 | 20 | 20 |
| Mobile phase flow rate: 0.3 ml/min. | | | | | |

Analysis Conditions 4

| Gradient | | | | | |
| --- | --- | --- | --- | --- | --- |
| Time (minutes) | 0.0 | 5.5 | 6.5 | 6.51 | 10.0 |
| Mobile phase (A) concentration (%) | 0 | 90 | 90 | 0 | 0 |
| Mobile phase flow rate: 0.3 ml/min. | | | | | |

Reference Example 1 Synthesis of trans,cis,cis-[PtCl(OH)(R,R-dach)(ox)]: Hexa-Coordinated Platinum Complex in which Y of Formula (XII) is Chlorine Atom N-chlorosuccinimide (66.8 mg) was dissolved in 14 ml of distilled water, a liquid obtained by suspending l-OHP (200 mg) in 6 ml of distilled water was added to the solution, and the mixture was stirred for 4 hours at room temperature in the dark. After completion of the reaction, insoluble matters in the reaction liquid were separated by filtration, the filtrate was concentrated under reduced pressure, and thereby a solid was obtained. The solid thus obtained was recrystallized from ethanol/water, and thus the title compound (114 mg) was obtained. $^1$H-NMR (D$_2$O): δ2.89-2.72 (2H, m), 2.15 (2H, d, J=12.2 Hz), 1.53-1.41 (4H, m), 0.97-0.90 (2H, m), MS(ESI):450 (M+1), 451 (M+2), purity (HPLC, analysis conditions 2): 99.4%.

Example 1 Production of Example 1 Compound (Conjugate of Block Copolymer Comprising Methoxy Polyethylene Glycol Moiety Having Molecular Weight of 12,000 and Polyaspartic Acid Moiety Having Polymerization Number of about 43, with trans,cis,cis-[PtCl(OH)(R,R-dach)ox]) and Phenylalanine Benzyl Ester; in Formula (I), R$_1$=Me (Methyl Group), R$_2$=Trimethylene Group, R$_3$=Ac (Acetyl Group), R$_4$=Residue Obtained by Eliminating H from Hydroxyl Group of Hexa-Coordinated Platinum Complex, R$_5$=Isopropylaminocarbonylisopropylamino Group, or Residue Obtained by Eliminating H from Amino Group of Phenylalanine Benzyl Ester (T=Hydrogen Atom), d+e+f+g+h+i+j=43, and a=273)

A methoxy polyethylene glycol-polyaspartic acid block copolymer (polymerization number of aspartic acid: about 43; 1.98 g) produced by the method described in JP 3268913 B and the hexa-coordinated platinum complex (899 mg) obtained in Reference Example 1 were dissolved in dimethylformamide (70 ml) at 35° C., and then dimethylaminopyridine (61 mg) was added thereto. The reaction liquid was adjusted to 25° C., and then diisopropylcarbodiimide (0.38 ml) was added thereto. After a lapse of 4 hours, phenylalanine benzyl ester hydrochloride (875 mg), diisopropylethylamine (0.52 ml), and diisopropylcarbodiimide (0.38 ml) were added thereto, and the resulting mixture was stirred for 18.5 hours. After completion of the reaction, the reaction liquid was slowly added to a mixed solvent of ethyl acetate (70 ml), ethanol (70 ml), and diisopropyl ether (700 ml), and the mixture was stirred at room temperature. Subsequently, the mixture was left to stand until the intended product precipitated, and the supernatant was removed. The precipitate thus obtained was further washed with ethanol/diisopropyl ether (1/4 (v/v); 100 ml), and a crude product (3.1 g) was collected by filtration. The crude product (1.4 g) thus obtained was dissolved in cold water (28 ml), and then the solution was passed through a column packed with an ion exchange resin (DOWEX 50 (H$^+$) manufactured by The Dow Chemical Company; 14 ml) and was eluted with cold water (40 ml). The eluted fraction thus obtained was freeze-dried, and thereby the title compound (1.04 g) was obtained. The drug content of the title compound thus obtained was 21.5% (mass fraction). Furthermore, the title compound was dissolved in water to a concentration of 1 mg/ml, and the particle size was measured. The particle size was 33 nm, and the compound formed micelles.

Example 2 Production of Example 2 Compound
(Conjugate of Block Copolymer Comprising
Methoxy Polyethylene Glycol Moiety Having
Molecular Weight of 12,000 and Polyaspartic Acid
Moiety Having Polymerization Number of about
43, with trans,cis,cis-[PtCl(OH)(R,R-dach)(ox)]; in
Formula (I), $R_1$=Me (Methyl Group),
$R_2$=Trimethylene Group, $R_3$=Ac (Acetyl Group),
$R_4$=Residue Obtained by Eliminating H from
Hydroxyl Group of Hexa-Coordinated Platinum
Complex,
$R_5$=Isopropylaminocarbonylisopropylamino Group,
d+e+f+g+h+i+j=43, and a=273)

A methoxy polyethylene glycol-polyaspartic acid block copolymer (polymerization number of aspartic acid: about 43; 0.93 g) produced by the method described in JP 3268913 B and the hexa-coordinated platinum complex (633 mg) obtained in Reference Example 1 were dissolved in dimethylformamide (40 ml) at 35° C., and then dimethylaminopyridine (29 mg) was added thereto. The reaction liquid was adjusted to 25° C., subsequently diisopropylcarbodiimide (0.43 ml) was added thereto, and the mixture was stirred for 5.5 hours. After completion of the reaction, the reaction liquid was slowly added to a mixed solvent of ethyl acetate (40 ml), ethanol (40 ml), and diisopropyl ether (400 ml), and the mixture was stirred at room temperature. Subsequently, the mixture was left to stand until the intended product precipitated, and the supernatant was removed. The precipitate thus obtained was further washed with ethanol/diisopropyl ether (1/4 (v/v); 40 ml), and a crude product (1.5 g) was collected by filtration. The crude product (1.45 g) thus obtained was dissolved in cold water (29 ml), and then the solution was passed through a column packed with an ion exchange resin (DOWEX 50 (H$^+$) manufactured by The Dow Chemical Company; 14.5 ml) and was eluted with cold water (40 ml). The eluted fraction thus obtained was freeze-dried, and thereby the title compound (1.25 g) was obtained. The drug content of the title compound thus obtained was 31.1% (mass fraction). Furthermore, the title compound was dissolved in water to a concentration of 1 mg/ml, and the particle size was measured. However, the scattering intensity was weak, and it was suggested that the compound did not form micelles.

Example 3 Production of Example 3 Compound
(Conjugate of Block Copolymer Comprising
Methoxy Polyethylene Glycol Moiety Having
Molecular Weight of 12,000 and Polyglutamic Acid
Moiety Having Polymerization Number of about
22, with trans,cis,cis-[PtCl(OH)(R,R-dach)ox]) and
Phenylalanine Benzyl Ester; in Formula (VI),
$R_{11}$=Me (Methyl Group), $R_{19}$=Trimethylene Group,
$R_{20}$=Ac (Acetyl Group), $R_{21}$=Residue Obtained by
Eliminating H from Hydroxyl Group of Hexa-Coordinated Platinum Complex,
$R_{22}$=Isopropylaminocarbonylisopropylamino Group,
or Residue Obtained by Eliminating H from Amino
Group of Phenylalanine Benzyl Ester (T=Hydrogen
Atom), k+m+n=22, and b=273)

The title compound was obtained by a method similar to that of Example 1, using a block copolymer (1.18 g) comprising a methoxy polyethylene glycol moiety having a molecular weight of 12,000 and a polyglutamic acid moiety having a polymerization number of about 22, which had been produced by the method described in JP 4745664 B, phenylalanine benzyl ester hydrochloride (0.31 g), the hexa-coordinated platinum complex obtained in Reference Example 1 (0.32 g), diisopropylethylamine (0.18 ml), dimethylaminopyridine (21 mg), and diisopropylcarbodiimide (0.27 ml). The drug content of the title compound thus obtained was 9.9% (mass fraction). Furthermore, the title compound was dissolved in water to a concentration of 1 mg/ml, and the particle size was measured. The particle size was 17 nm, and the compound formed micelles.

Example 4 Production of Example 4 Compound
(Conjugate of Block Copolymer Comprising
Methoxy Polyethylene Glycol Moiety Having
Molecular Weight of 2,000 and Polyaspartic Acid
Moiety Having Polymerization Number of about
11, with trans,cis,cis-[PtCl(OH)(R,R-dach)ox]) and
Phenylalanine Benzyl Ester; in Formula (I), $R_1$=Me
(Methyl Group), $R_2$=Trimethylene Group, $R_3$=Ac
(Acetyl Group), $R_4$=Residue Obtained by Eliminating H from Hydroxyl Group of Hexa-Coordinated
Platinum Complex,
$R_5$=Isopropylaminocarbonylisopropylamino Group,
or Residue Obtained by Eliminating H from Amino
Group of Phenylalanine Benzyl Ester (T=Hydrogen
Atom), d+e+f+g+h+i+j=11, and a=46)

The title compound was obtained by a method similar to that of Example 1, using a block copolymer (0.61 g) comprising a methoxy polyethylene glycol moiety having a molecular weight of 2,000 and a polyaspartic acid moiety having a polymerization number of about 11, which had been produced by the method described in JP 3268913 B, the hexa-coordinated platinum complex obtained in Reference Example 1 (0.38 g), phenylalanine benzyl ester hydrochloride (0.35 g), diisopropylethylamine (0.21 ml), dimethylaminopyridine (24 mg), and diisopropylcarbodiimide (0.29 ml). The drug content of the title compound thus obtained was 14.8% (mass fraction). Furthermore, the title compound was dissolved in water to a concentration of 1 mg/ml, and the particle size was measured. The particle size was less than 10 nm, and the compound formed micelles.

Example 5 Production of Example 5 Compound
(Conjugate of Block Copolymer Comprising
Methoxy Polyethylene Glycol Moiety Having
Molecular Weight of 40,000 and Polyaspartic Acid
Moiety Having Polymerization Number of about
41, with trans,cis,cis-[PtCl(OH)(R,R-dach)ox]) and
Phenylalanine Benzyl Ester; in Formula (I), $R_1$=Me
(Methyl Group), $R_2$=Trimethylene Group, $R_3$=Ac
(Acetyl Group), $R_4$=Residue Obtained by Eliminating H from Hydroxyl Group of Hexa-Coordinated
Platinum Complex,
$R_5$=Isopropylaminocarbonylisopropylamino Group,
or Residue Obtained by Eliminating H from Amino
Group of Phenylalanine Benzyl Ester (T=Hydrogen
Atom), d+e+f+g+h+i+j=41, and a=909)

The title compound was obtained by a method similar to that of Example 1, using a block copolymer (1.00 g) comprising a methoxy polyethylene glycol moiety having a molecular weight of 40,000 and a polyaspartic acid moiety having a polymerization number of about 41, which had been produced by the method described in JP 3268913 B, the hexa-coordinated platinum complex obtained in Reference Example 1 (0.17 g), phenylalanine benzyl ester hydrochloride (0.19 g), diisopropylethylamine (0.12 ml), dimethylaminopyridine (11 mg), and diisopropylcarbodiimide (0.15 ml). The drug content of the title compound thus obtained was 7.0% (mass fraction). Furthermore, the title compound was dissolved in water to a concentration of 1 mg/ml, and the particle size was measured. The particle size was 80 nm, and the compound formed micelles.

Reference Example 2 Block Copolymer Comprising Methoxy Polyethylene Glycol Moiety Having Molecular Weight of 12,000 and Moiety Having Structure in which Phenylalanine was Bonded to Side Chain of Polyaspartic Acid Having Polymerization Number of about 43

A methoxy polyethylene glycol-polyaspartic acid block copolymer (polymerization number of aspartic acid: about 43; 3.03 g) produced by the method described in JP 3268913 B was dissolved in dimethylformamide (25 ml) at 35° C., and phenylalanine benzyl ester hydrochloride (2.33 g), diisopropylethylamine (1.42 ml), dimethylaminopyridine (93 mg), and dimethylformamide (5 ml) were added thereto. The liquid temperature was cooled to 25° C., and then diisopropylcarbodiimide (2.34 ml) was added to the mixture. The mixture was stirred for 18 hours at the same temperature, subsequently the temperature was raised to 30° C., and the mixture was stirred for 5 hours. Subsequently, diisopropylcarbodiimide (0.23 ml) was further added thereto, and the mixture was stirred for 2 hours. After completion of the reaction, the mixture was slowly added to a mixed solvent of ethanol (60 ml) and diisopropyl ether (240 ml), and the resulting mixture was stirred at room temperature. Subsequently, the mixture was left to stand until the intended product precipitated, and the supernatant was removed. The precipitate thus obtained was collected by filtration and was dried under reduced pressure, and thus a crude product (4.6 g) was obtained. The crude product (4.6 g) thus obtained was dissolved in a mixed liquid of acetonitrile (60 ml) and water (20 ml), and the solution was passed through a column packed with an ion exchange resin (DOWEX 50 (H$^+$) manufactured by The Dow Chemical Company; 40 ml) and was eluted with a 20% aqueous solution of acetonitrile (110 ml). Acetonitrile was removed by concentrating the eluted fraction thus obtained under reduced pressure, and the resultant was freeze-dried. Thus, a benzyl-protected form of the title compound (4.52 g) was obtained. The benzyl-protected form (3.14 g) thus obtained was dissolved in dimethylformamide (63 ml) at 35° C., hydrous Pd/C (10%) (688 mg) was added thereto, and the mixture was stirred for 22 hours at 33° C. in a hydrogen atmosphere. After completion of the reaction, the mixture was treated with a metal scavenger (SiliaMetS TAAcOH), the mixture was filtered using Celite, and the filtrate was slowly added dropwise to a mixed solvent of heptanes (570 ml) and ethyl acetate (114 ml). The mixture was stirred at room temperature and then was left to stand until the intended product precipitated, and the supernatant was removed. The processes of adding a mixed solvent of heptanes and ethyl acetate to the precipitate thus obtained and removing the supernatant was repeated two times, and a precipitate was collected by filtration and dried under reduced pressure. Thus, the title compound (1.8 g) was obtained.

Example 6 Production of Example 6 Compound (Conjugate of Block Copolymer Comprising Methoxy Polyethylene Glycol Moiety Having Molecular Weight of 12,000 and Moiety Having Structure in which Phenylalanine was Bonded to Side Chain of Polyaspartic Acid Having Polymerization Number of about 43, with trans,cis,cis-[PtCl(OH)(R,R-dach)(ox)]; in Formula (I), $R_1$=Me (Methyl Group), $R_2$=Trimethylene Group, $R_3$=Ac (Acetyl Group), $R_4$=Structure of (i) of Formula (II) (W=Residue Obtained by Eliminating H from Hydroxyl Group of Hexa-Coordinated Platinum Complex, or Isopropylaminocarbonylisopropylamino Group, T=Hydrogen Atom), $R_5$=Isopropylaminocarbonylisopropylamino Group, d+e+f+g+h+i+j=43, and a=273)

The block copolymer (0.6 g) produced in Reference Example 2, comprising a methoxy polyethylene glycol moiety and a moiety having a structure in which phenylalanine was bonded to a side chain of a polyaspartic acid having a polymerization number of about 43, and the hexa-coordinated platinum complex (460 mg) obtained in Reference Example 1 were dissolved in dimethylformamide (30 ml) at 35° C., and then dimethylaminopyridine (12 mg) was added to the solution. The reaction liquid was adjusted to 30° C., and then diisopropylcarbodiimide (0.31 ml) was added thereto. After a lapse of 21 hours, diisopropylcarbodiimide (0.31 ml) was added thereto. After 3 hours, the temperature of the solution was raised to 35° C., and the solution was stirred for 2 hours. After completion of the reaction, the reaction liquid was slowly added to a mixed solvent of ethanol (43 ml) and diisopropyl ether (257 ml), and the mixture was stirred at room temperature. Subsequently, the mixture was left to stand until the intended product precipitated, and the supernatant was removed. Ethanol/diisopropyl ether (1/6 (v/v); 150 ml) was further added to the precipitate thus obtained, and a crude product (807 mg) was collected by filtration. The crude product (785 mg) thus obtained was dissolved in cold water (80 ml), and then centrifugal ultrafiltration was performed using a VIVASPIN 20 (MWCO: 3 kDa) (Sartorius AG) to remove low molecular weight compounds. The solution obtained after purification was freeze-dried, and thereby the title compound (424 mg) was obtained. The drug content of the title compound thus obtained was 14.1% (mass fraction). Furthermore, the title compound was dissolved in water to a concentration of 1 mg/ml, and the particle size was measured. The particle size was 68 nm, and the compound formed micelles.

Example 7 Production of Example 7 Compound (Conjugate of Block Copolymer Comprising Methoxy Polyethylene Glycol Moiety Having Molecular Weight of 2,000 and Polyglutamic Acid Moiety Having Polymerization Number of about 10, with trans,cis,cis-[PtCl(OH)(R,R-dach)ox]) and Phenylalanine Benzyl Ester; in Formula (VI), $R_{11}$=Me (Methyl Group), $R_{19}$=Trimethylene Group, $R_{20}$=Ac (Acetyl Group), $R_{21}$=Residue Obtained by Eliminating H from Hydroxyl Group of Hexa-Coordinated Platinum Complex, $R_{22}$=Isopropylaminocarbonylisopropylamino Group, or Residue Obtained by Eliminating H from Amino Group of Phenylalanine Benzyl Ester (T=Hydrogen Atom), k+m+n=10, and b=46)

A block copolymer comprising a methoxy polyethylene glycol moiety having a molecular weight of 2,000 and a polyglutamic acid moiety having a polymerization number of about 10 (polymerization number of glutamic acid: about 10; 750 mg), which had been produced by the method described in JP 4745664 B, was dissolved in dimethylformamide (29 ml) at 35° C., and then the hexa-coordinated platinum complex (400 mg) obtained in Reference Example 1 and dimethylaminopyridine (27.6 mg) were added to the solution. The reaction liquid was adjusted to 25° C., and then diisopropylcarbodiimide (0.17 ml) was added thereto. After a lapse of 5 hours, phenylalanine benzyl ester hydrochloride (390 mg), diisopropylethylamine (0.38 ml), and diisopropylcarbodiimide (0.34 ml) were added thereto, and the mixture was stirred for 17.5 hours. Subsequently, isopropylcarbodiimide (0.17 ml) was added thereto, and the resulting mixture was stirred for another 5 hours. After completion of the reaction, the reaction liquid was slowly added to a mixed solvent of ethyl acetate (31 ml) and diisopropyl ether (589 ml), and the mixture was stirred at room temperature. Subsequently, the mixture was left to stand until the intended product precipitated, and the supernatant was removed. Subsequently, a mixed solvent of ethyl acetate (31 ml) and diisopropyl ether (589 ml) was added to the residue, and the mixture was stirred overnight. Subsequently, the supernatant liquid was removed, the residue was dried under reduced pressure, and then a crude product (1.52 g) was obtained. The crude product thus obtained was dissolved in cold water (72 ml), and then purification was performed using a VIVASPIN TURBO 15 (MWCO: 10 kDa) (Sartorius AG). The solution thus obtained was freeze-dried, and thereby the title compound (994 mg) was obtained. The drug content of the title compound thus obtained was 14.5% (mass fraction). Furthermore, the title compound was dissolved in water to a concentration of 5 mg/ml, and the particle size was measured. The particle size was 9.9 nm, and the compound formed micelles.

Example 8 Production of Example 8 Compound (Conjugate of Block Copolymer Comprising Methoxy Polyethylene Glycol Moiety Having Molecular Weight of 2,000 and Polyglutamic Acid Moiety Having Polymerization Number of about 8, with trans,cis,cis-[PtCl(OH)(R,R-dach)ox]) and Phenylalanine Benzyl Ester; in Formula (VI), $R_{11}$=Me (Methyl Group), $R_{19}$=Trimethylene Group, $R_{20}$=Ac (Acetyl Group), $R_{21}$=Residue Obtained by Eliminating H from Hydroxyl Group of Hexa-Coordinated Platinum Complex, $R_{22}$=Isopropylaminocarbonylisopropylamino Group, or Residue Obtained by Eliminating H from Amino Group of Phenylalanine Benzyl Ester (T=Hydrogen Atom), k+m+n=8, and b=46)

A block copolymer comprising a methoxy polyethylene glycol moiety having a molecular weight of 2,000 and a polyglutamic acid moiety having a polymerization number of about 8 (polymerization number of glutamic acid: about 8; 1001 mg), which had been produced by the method described in JP 4745664 B, was dissolved in dimethylformamide (36 ml) at 35° C., and then the hexa-coordinated platinum complex (461 mg) obtained in Reference Example 1 and dimethylaminopyridine (31.5 mg) were added to the solution. The reaction liquid was adjusted to 25° C., and then diisopropylcarbodiimide (0.20 ml) was added thereto. After a lapse of 4.5 hours, phenylalanine benzyl ester hydrochloride (450 mg), diisopropylethylamine (0.44 ml), and diisopropylcarbodiimide (0.40 ml) were added thereto, and the mixture was stirred for 16 hours. Subsequently, diisopropylcarbodiimide (0.20 ml) was added thereto, and the resulting mixture was stirred for another 4 hours. After completion of the reaction, the reaction liquid was slowly added to a mixed solvent of ethyl acetate (38 ml) and diisopropyl ether (722 ml), and the mixture was stirred at room temperature. Subsequently, the mixture was left to stand until the intended product precipitated, and the supernatant was removed. Subsequently, a mixed solvent of ethyl acetate (38 ml) and diisopropyl ether (722 ml) was added to the residue, and the mixture was stirred overnight. Subsequently, the supernatant liquid was removed, the residue was dried under reduced pressure, and then a crude product (1.77 g) was obtained. The crude product (1.68 g) thus obtained was dissolved in cold water (72 ml), and then purification was performed using a VIVASPIN TURBO 15 (MWCO: 10 kDa) (Sartorius AG). The solution thus obtained was freeze-dried, and thereby the title compound (1270 mg) was obtained. The drug content of the title compound thus obtained was 14.3% (mass fraction). Furthermore, the title compound was dissolved in water to a concentration of 5 mg/ml, and the particle size was measured. The particle size was 9.6 nm, and the compound formed micelles.

Reference Example 3 Synthesis of trans,cis,cis-[PtCl(OH)(R,R-dach)Cl$_2$]: Hexa-Coordinated Platinum Complex in which Y of Formula (XIII) was Chlorine Atom N-chlorosuccinimide (534 mg) was dissolved in 50 ml of distilled water, and the solution was added to a liquid obtained by suspending Pt(R,R-dach)Cl$_2$ (1.52 g) produced according to the description of J. Med. Chem., 52, 5474-5484 (2009) in 500 ml of tetrahydrofuran. The mixture was stirred for 3 hours at room temperature in the dark. After completion of the reaction, any insoluble matters in the reaction liquid were separated by filtration, and the filtrate was concentrated under reduced pressure to obtain a solid. The solid thus obtained was suspended in ethanol, and the suspension was collected again by filtration. Thus, the intended product (1.55 g) was obtained. $^1$H-NMR (DMSO-d$_6$): δ7.53-7.29 (2H, m), 6.89-6.78 (2H, m), 2.75-2.60 (2H, m), 2.10-2.00 (2H, m), 1.47 (2H, d, J=8.0 Hz), 1.10-0.93 (2H, m), MS(ESI):433 (M+1), purity (HPLC, analysis conditions 2): 98.1%.

Example 9 Production of Example 9 Compound (Conjugate of Block Copolymer Comprising Methoxy Polyethylene Glycol Moiety Having Molecular Weight of 12,000 and Polyaspartic Acid Moiety Having Polymerization Number of about 43, with trans,cis,cis-[PtCl(OH)(R,R-dach)Cl$_2$] and Phenylalanine Benzyl Ester; in Formula (I), $R_1$=Me (Methyl Group), $R_2$=Trimethylene Group, $R_3$=Ac (Acetyl Group), $R_4$=Residue Obtained by Eliminating H from Hydroxyl Group of Hexa-Coordinated Platinum Complex, $R_5$=Isopropylaminocarbonylisopropylamino Group or Residue Obtained by Eliminating H from Amino Group of Phenylalanine Benzyl Ester (T=Hydrogen Atom), d+e+f+g+h+i+j=43, and a=273)

A methoxy polyethylene glycol-polyaspartic acid block copolymer (polymerization number of aspartic acid: about 43; 0.577 g) produced by the method described in JP 3268913 B and the hexa-coordinated platinum complex (251 mg) obtained in Reference Example 3 were dissolved in dimethylformamide (20 ml) at 35° C., and then dimethylaminopyridine (17.8 mg) was added to the solution. The reaction liquid was adjusted to 25° C., and then diisopropylcarbodiimide (0.112 ml) was added thereto. After a lapse of 4.5 hours, phenylalanine benzyl ester hydrochloride (254.8 mg), diisopropylethylamine (0.112 ml), and diisopropylcarbodiimide (0.152 ml) were added thereto, and the resulting mixture was stirred for 18.5 hours. After completion of the reaction, the reaction liquid was slowly added to a mixed solvent of ethyl acetate (20 ml), ethanol (20 ml), and diisopropyl ether (160 ml), and the mixture was stirred at room temperature. Subsequently, the mixture was left to stand until the intended product precipitated, and the supernatant was removed. The precipitate thus obtained was further washed with ethanol/diisopropyl ether (1/4 (v/v); 50 ml), and a crude product (0.791 g) was collected by filtration. The crude product (0.7 g) thus obtained was dissolved in a 10% aqueous solution of acetonitrile (30 ml), and then purification was performed using a VIVASPIN TURBO 15 (MWCO: 10 kDa) (Sartorius AG). The solution thus obtained was freeze-dried, and thereby the title compound (0.68 g) was obtained. The drug content of the title compound thus obtained was 6.4% (mass fraction). Furthermore, the title compound was dissolved in water to a concentration of 1 mg/ml, and the particle size was measured. The particle size was 87 nm, and the compound formed micelles.

Example 10 Production of Example 10 Compound (Conjugate of Block Copolymer Comprising Methoxy Polyethylene Glycol Moiety Having Molecular Weight of 12,000 and Moiety Having Structure in which Phenylalanine was Bonded to Side Chain of Polyaspartic Acid Having Polymerization Number of about 43, with trans,cis,cis-[PtCl(OH)(R,R-dach)Cl$_2$]; in Formula (I), R$_1$=Me (Methyl Group), R$_2$=Trimethylene Group, R$_3$=Ac (Acetyl Group), R$_4$=Structure of (i) of Formula (II) (W=Residue Obtained by Eliminating H from Hydroxyl Group of Hexa-Coordinated Platinum Complex, or Isopropylaminocarbonylisopropylamino Group, T=Hydrogen Atom), R$_5$=Isopropylaminocarbonylisopropylamino Group, d+e+f+g+h+i+j=43, and a=273)

The block copolymer (390 mg) produced in Reference Example 2, comprising a methoxy polyethylene glycol moiety and a moiety having a structure in which phenylalanine was bonded to a side chain of a polyaspartic acid having a polymerization number of about 43, and the hexa-coordinated platinum complex (225 mg) obtained in Reference Example 3 were dissolved in dimethylformamide (5 ml) at 35° C., and then dimethylaminopyridine (8 mg) was added to the solution. The reaction liquid was adjusted to 30° C., and then diisopropylcarbodiimide (0.20 ml) was added thereto. After a lapse of 23 hours, diisopropylcarbodiimide (0.10 ml) was further added thereto. After one hour, the temperature of the solution was raised to 35° C., and the solution was stirred for 2 hours. After completion of the reaction, the reaction liquid was slowly added to a mixed solvent of ethyl acetate (6 ml), ethanol (6 ml), and diisopropyl ether (48 ml), and the mixture was stirred at room temperature. Subsequently, the mixture was left to stand until the intended product precipitated, and the supernatant was removed. A mixed solvent of ethyl acetate (1 ml), ethanol (1 ml), and diisopropyl ether (8 ml) was further added to the precipitate thus obtained, and a crude product (408 mg) was collected by filtration. The crude product (399 mg) thus obtained was dissolved in a 10% aqueous solution of acetonitrile (16 ml), and then centrifugal ultrafiltration was performed using a VIVASPIN TURBO 15 (MWCO: 10 kDa) (Sartorius AG) to remove low molecular weight compounds. The solution obtained after purification was freeze-dried, and thereby the title compound (241 mg) was obtained. The drug content of the title compound thus obtained was 8.2% (mass fraction). Furthermore, the title compound was dissolved in water to a concentration of 1 mg/ml, and the particle size was measured. The particle size was 17 nm, and the compound formed micelles.

Reference Example 4 Block Copolymer Comprising Methoxy Polyethylene Glycol Moiety Having Molecular Weight of 2,000 and Moiety Having Structure in which Phenylalanine was Bonded to Side Chain of Polyaspartic Acid Having Polymerization Number of about 12

A methoxy polyethylene glycol-polyaspartic acid block copolymer (polymerization number of aspartic acid: about 12; 2.04 g), which had been produced by the method described in JP 3268913 B, was dissolved in dimethylformamide (20 ml) at 35° C. The liquid temperature was cooled to 25° C., and then phenylalanine benzyl ester hydrochloride (2.17 g; 1.05 equivalents with respect to carboxyl groups), diisopropylethylamine (1.33 ml), dimethylaminopyridine (86 mg), and diisopropylcarbodiimide (2.19 ml) were added to the solution. The mixture was stirred for 15 hours at the same temperature, and then the temperature was raised to 30° C. Diisopropylcarbodiimide (0.22 ml) was further added thereto, and the mixture was stirred for another 2 hours. After completion of the reaction, the reaction mixture was slowly added to a mixed solvent of ethyl acetate (20 ml) and diisopropyl ether (380 ml), and the mixture was stirred at room temperature. Subsequently, the mixture was left to stand until the intended product precipitated. Ethyl acetate/diisopropyl ether (19/1 (v/v); 400 ml) was further added to the precipitate thus obtained, and a crude product (5.4 g) was collected by filtration. The crude product (5.4 g) thus obtained was dissolved in a mixed liquid of acetonitrile (18 ml) and water (12 ml), and the solution was passed through a column packed with an ion exchange resin (DOWEX 50 (H$^+$) manufactured by The Dow Chemical Company; 70 ml) and was eluted with a 60% aqueous solution of acetonitrile (225 ml). The eluted fraction thus obtained was concentrated under reduced pressure to remove acetonitrile, and the residue was freeze-dried. Thereby, a benzyl-protected form of the title compound (3.8 g) was obtained. The benzyl-protected form (3.75 g) thus obtained was dissolved in dimethylformamide (67 ml), hydrous Pd/C (5%) (375 mg) was added thereto, and the mixture was stirred for 20 hours at room temperature in a hydrogen atmosphere. After completion of the reaction, the reaction liquid was treated with a metal scavenger (SiliaMetS TAAcOH), and the resultant was filtered using a filter made of hydrophilic polytetrafluoroethylene. Subsequently, the filtrate was slowly added dropwise to diisopropyl ether (1340 ml), and the mixture was stirred at room temperature. Subsequently, the mixture was left to stand until the intended product precipitated, and the supernatant was removed. Diisopropyl ether (1005 ml) was added to the precipitate thus obtained, and the precipitate was collected by filtration and dried under reduced pressure. Thus, the title compound (2.5 g) was obtained.

Example 11 Production of Example 11 Compound
(Conjugate of Block Copolymer Comprising
Methoxy Polyethylene Glycol Moiety Having
Molecular Weight of 2,000 and Moiety Having
Structure in which Phenylalanine was Bonded to
Side Chain of Polyaspartic Acid Having Polymerization Number of about 12, with trans,cis,cis-[PtCl(OH)(R,R-dach)Cl$_2$]; in Formula (I), $R_1$=Me
(Methyl Group), $R_2$=Trimethylene Group, $R_3$=Ac
(Acetyl Group), $R_4$=Structure of (i) of Formula (II)
(W=Residue Obtained by Eliminating H from
Hydroxyl Group of Hexa-Coordinated Platinum
Complex, or Isopropylaminocarbonylisopropylamino Group, T=Hydrogen Atom),
$R_5$=Isopropylaminocarbonylisopropylamino Group,
d+e+f+g+h+i+j=12, and a=46)

The block copolymer produced by the method of Reference Example 4 (0.3 g), comprising a methoxy polyethylene glycol moiety and a moiety having a structure in which phenylalanine was bonded to a side chain of polyaspartic acid having a polymerization number of about 12, and the hexa-coordinated platinum complex (303 mg) obtained in Reference Example 3 were dissolved in dimethylformamide (15 ml) at 25° C., and then dimethylaminopyridine (17 mg) and diisopropylcarbodiimide (0.22 ml) were added to the solution. The mixture was stirred for 15 hours. After completion of the reaction, the reaction liquid was slowly added to a mixed solvent of ethyl acetate (15 ml) and diisopropyl ether (135 ml), and the mixture was stirred at room temperature. Subsequently, the mixture was left to stand until the intended product precipitated, and the supernatant was removed. Ethyl acetate/diisopropyl ether (1/9 (v/v); 150 ml) was added to the precipitate thus obtained, and a crude product (550 mg) was collected by filtration. The crude product (550 mg) thus obtained was dissolved in cold water (35 ml), and then centrifugal ultrafiltration was performed using a VIVASPIN TURBO 15 (MWCO: 3 kDa) (Sartorius AG) to remove low molecular weight compounds. The solution obtained after purification was freeze-dried, and thereby, the title compound (173 mg) was obtained. The drug content of the title compound thus obtained was 19.3% (mass fraction). Furthermore, the title compound was dissolved in water to a concentration of 1 mg/ml, and the particle size was measured. The particle size was 21 nm, and the compound formed micelles.

Reference Example 5 Block Copolymer
Comprising Methoxy Polyethylene Glycol Moiety
Having Molecular Weight of 2,000 and Moiety
Having Structure in which Phenylalanine was
Bonded to Side Chain of Polyaspartic Acid Having
Polymerization Number of about 12

A methoxy polyethylene glycol-polyaspartic acid block copolymer (polymerization number of aspartic acid: about 12; 2.05 g) produced by the method described in JP 3268913 B was dissolved in dimethylformamide (21 ml) at 35° C., and phenylalanine benzyl ester hydrochloride (2.25 g; 1.05 equivalents with respect to carboxyl groups), diisopropylethylamine (1.35 ml), and dimethylaminopyridine (90 mg) were added to the solution. The liquid temperature was cooled to 25° C., and then diisopropylcarbodiimide (2.26 ml) was added thereto. The mixture was stirred for 19 hours at the same temperature, and then the temperature was raised to 30° C. Next, diisopropylcarbodiimide (0.23 ml) was further added thereto, and the mixture was stirred for 5.5 hours. After completion of the reaction, the reaction mixture was slowly added to a mixed solvent of ethanol (20 ml) and diisopropyl ether (380 ml), and the mixture was stirred at room temperature. The supernatant was removed, and the residue was dried under reduced pressure to obtain a crude product (4.6 g). The crude product (4.6 g) thus obtained was dissolved in a mixed liquid of acetonitrile (18 ml) and water (12 ml), and the solution was passed through a column packed with an ion exchange resin (DOWEX 50 (H$^+$) manufactured by The Dow Chemical Company; 69 ml) and was eluted with a 60% aqueous solution of acetonitrile (375 ml). The eluted fraction thus obtained was concentrated under reduced pressure to remove acetonitrile, and the residue was freeze-dried. Thereby, a benzyl-protected form of the title compound (4.5 g) was obtained. The benzyl-protected form (4.5 g) thus obtained was dissolved in a mixed solvent of dimethylformamide (89 ml) and acetic acid (4.5 ml) at 35° C., hydrous Pd/C (10%) (450 mg) was added to the solution, and the mixture was stirred at 30° C. for 67 hours in a hydrogen atmosphere. After completion of the reaction, the reaction mixture was treated with a metal scavenger (SiliaMetS TAAcOH), and the treated reaction mixture was filtered using Celite. The filtrate was slowly added dropwise to diisopropyl ether (1,800 ml), and the mixture was stirred at room temperature. The supernatant was removed, and the processes of adding diisopropyl ether to the precipitate thus obtained and removing the supernatant were repeated two times. The residue was dried under reduced pressure, and thereby, the title compound (1.7 g) was obtained.

Example 12 Production of Example 12 Compound
(Conjugate of Block Copolymer Comprising
Methoxy Polyethylene Glycol Moiety Having
Molecular Weight of 2,000 and Moiety Having
Structure in which Phenylalanine was Bonded to
Side Chain of Polyaspartic Acid Having Polymerization Number of about 12, with trans,cis,cis-[PtCl(OH)(R,R-dach)(ox)]; in Formula (I), $R_1$=Me
(Methyl Group), $R_2$=Trimethylene Group, $R_3$=Ac
(Acetyl Group), $R_4$=Structure of (i) of Formula (II)
(W=Residue Obtained by Eliminating H from
Hydroxyl Group of Hexa-Coordinated Platinum
Complex, or Isopropylaminocarbonylisopropylamino Group, T=Hydrogen Atom),
$R_5$=Isopropylaminocarbonylisopropylamino Group,
d+e+f+g+h+i+j=12, and a=46)

The block copolymer (733 mg) produced in Reference Example 5, comprising a methoxy polyethylene glycol moiety and a moiety having a structure in which phenylalanine was bonded to a side chain of a polyaspartic acid having a polymerization number of about 12, and the hexa-coordinated platinum complex (756 mg) obtained in Reference Example 1 were dissolved in dimethylformamide (78 ml) at 35° C., and then dimethylaminopyridine (21 mg) was added thereto. The reaction liquid was adjusted to 30° C., subsequently diisopropylcarbodiimide (0.52 ml), was added, and the mixture was stirred. After a lapse of 20 hours, diisopropylcarbodiimide (0.52 ml) was further added thereto, the temperature of the solution was raised to 35° C., and the solution was stirred for 2 hours. After completion of the reaction, the reaction liquid was slowly added to a mixed solvent of ethyl acetate (78 ml) and diisopropyl ether (1482 ml), and the mixture was stirred at room temperature. Subsequently, the mixture was left to stand until the intended product precipitated, and the supernatant was removed.

Ethyl acetate/diisopropyl ether (1/19 (v/v); 780 ml) was further added to the precipitate thus obtained, and a crude product (1.30 g) was collected by filtration. The crude product (642 mg) thus obtained was dissolved in a 5% aqueous solution of acetonitrile (36 ml), and then centrifugal ultrafiltration was performed using a VIVASPIN TURBO 15 (MWCO: 10 kDa) (Sartorius AG) to remove low molecular weight compounds. The solution obtained after purification was freeze-dried, and thereby the title compound (389 mg) was obtained. The drug content of the title compound thus obtained was 18.1% (mass fraction). Furthermore, the title compound was dissolved in water to a concentration of 1 mg/ml, and the particle size was measured. The particle size was 10 nm, and the compound formed micelles.

Example 13 Production of Example 13 Compound (Conjugate of Block Copolymer Comprising Methoxy Polyethylene Glycol Moiety Having Molecular Weight of 2,000 and Moiety Having Structure in which Phenylalanine was Bonded to Side Chain of Polyaspartic Acid Having Polymerization Number of about 12, with trans,cis,cis-[PtCl(OH)(R,R-dach)(ox)]; in Formula (I), $R_1$=Me (Methyl Group), $R_2$=Trimethylene Group, $R_3$=Ac (Acetyl Group), $R_4$=Structure of (i) of Formula (II) (W=Residue Obtained by Eliminating H from Hydroxyl Group of Hexa-Coordinated Platinum Complex, or Isopropylaminocarbonylisopropylamino Group, T=Hydrogen Atom), $R_5$=Isopropylaminocarbonylisopropylamino Group, d+e+f+g+h+i+j=12, and a=46)

The block copolymer (0.9 g) produced in Reference Example 4, comprising a methoxy polyethylene glycol moiety and a moiety having a structure in which phenylalanine was bonded to a side chain of a polyaspartic acid having a polymerization number of about 12, was dissolved in dimethylformamide (39 ml) at 35° C. The reaction liquid was adjusted to 30° C., subsequently the hexa-coordinated platinum complex (532 mg) obtained in Reference Example 1, dimethylaminopyridine (24 mg), and diisopropylcarbodiimide (0.61 ml) were added thereto, and the mixture was stirred. After a lapse of 45 hours, diisopropylcarbodiimide (0.61 ml) was further added thereto, the temperature of the solution was raised to 35° C., and the solution was stirred for 3 hours. After completion of the reaction, the reaction liquid was slowly added to a mixed solvent of ethyl acetate (39 ml) and diisopropyl ether (351 ml), and the mixture was stirred at room temperature. Subsequently, the mixture was left to stand until the intended product precipitated, and the supernatant was removed. Ethyl acetate/diisopropyl ether (1/9 (v/v); 390 ml) was further added to the precipitate thus obtained, and a crude product (1.27 g) was collected by filtration. The crude product (1.2 g) thus obtained was dissolved in a 5% aqueous solution of acetonitrile (36 ml), and the centrifugal ultrafiltration was performed using a VIVASPIN TURBO 15 (MWCO: 10 kDa) (Sartorius AG) to remove low molecular weight compounds. The solution obtained after purification was freeze-dried, and thereby the title compound (863 mg) was obtained. The drug content of the title compound thus obtained was 14.4% (mass fraction). Furthermore, the title compound was dissolved in water to a concentration of 5 mg/ml, and the particle size was measured. The particle size was 13 nm, and the compound formed micelles.

Reference Example 6 Block Copolymer Having Methoxy Polyethylene Glycol Moiety Having Molecular Weight of 2,000 and Moiety Having Structure in which Phenylalanine was Bonded to Side Chain of Polyaspartic Acid Having Polymerization Number of about 7

A methoxy polyethylene glycol-polyaspartic acid block copolymer (polymerization number of aspartic acid: about 7; 1.0 g) produced by the method described in JP 3268913 B was dissolved in dimethylformamide (10 ml) at 35° C., and phenylalanine benzyl ester hydrochloride (770 mg), diisopropylethylamine (0.47 ml), and dimethylaminopyridine (31 mg) were added to the solution. The liquid temperature was cooled to 25° C., and then diisopropylcarbodiimide (0.77 ml) was added thereto. The mixture was stirred for 19 hours at the same temperature, and then the temperature was raised to 30° C. Next, diisopropylcarbodiimide (0.08 ml) was further added thereto, and the mixture was stirred for 4 hours. After completion of the reaction, the reaction mixture was slowly added to a mixed solvent of ethyl acetate (10 ml) and diisopropyl ether (190 ml), and the mixture was stirred at room temperature. The supernatant was removed, and ethyl acetate/diisopropyl ether (1/19 (v/v); 100 ml) was added to the residue. The mixture was stirred at room temperature, and then the supernatant was removed. The residue was dried under reduced pressure, and a crude product (2.0 g) was obtained. The crude product (2.0 g) thus obtained was dissolved in a mixed liquid of acetonitrile (7.5 ml) and water (7.5 ml), and the solution was passed through a column packed with an ion exchange resin (DOWEX 50 ($H^+$) manufactured by The Dow Chemical Company; 30 ml) and was eluted with a 50% aqueous solution of acetonitrile (120 ml). The elution fraction thus obtained was concentrated under reduced pressure to remove acetonitrile, and the residue was freeze-dried. Thereby, a benzyl-protected form of the title compound (1.56 g) was obtained. The benzyl-protected form (1.54 g) thus obtained was dissolved in dimethylformamide (30 ml) at 35° C., and hydrous Pd/C (5%) (159 mg) was added thereto. The mixture was stirred at 30° C. for 19 hours in a hydrogen atmosphere. Subsequently, the mixture was treated with activated carbon and was filtered using a filter paper. The filtrate was concentrated under reduced pressure to remove the solvent. Next, the residue was dissolved in N-methylpyrrolidone at 30° C., and hydrous Pd/C (5%) (159 mg) was added to the solution. The mixture was stirred at 30° C. for 14 hours in a hydrogen atmosphere. After completion of the reaction, the reaction mixture was treated with activated carbon and was filtered using a filter paper. The filtrate was slowly added dropwise to diisopropyl ether (500 ml), and the mixture was stirred at room temperature. The supernatant was removed, and diisopropyl ether was added to a precipitate thus obtained. The supernatant was removed, and the residue was dried under reduced pressure. The residue thus obtained was dissolved in water and freeze-dried, and thus the title compound (1.0 g) was obtained.

Example 14 Production of Example 14 Compound (Conjugate of Block Copolymer Comprising Methoxy Polyethylene Glycol Moiety Having Molecular Weight of 2,000 and Moiety Having Structure in which Phenylalanine was Bonded to Side Chain of Polyaspartic Acid Having Polymerization Number of about 7, with trans,cis,cis-[PtCl(OH)(R,R-dach)(ox)]; in Formula (I), $R_1$=Me (Methyl Group), $R_2$=Trimethylene Group, $R_3$=Ac (Acetyl Group), $R_4$=Structure of (i) of Formula (II) (W=Residue Obtained by Eliminating H from Hydroxyl Group of Hexa-Coordinated Platinum Complex, or Isopropylaminocarbonylisopropylamino Group, T=Hydrogen Atom), $R_5$=Isopropylaminocarbonylisopropylamino Group, $d+e+f+g+h+i+j=7$, and $a=46$)

The block copolymer (838 mg) produced in Reference Example 6, comprising a methoxy polyethylene glycol moiety and a moiety having a structure in which phenylalanine was bonded to a side chain of a polyaspartic acid having a polymerization number of about 7, and the hexa-coordinated platinum complex (416 mg) obtained in Reference Example 1 were dissolved in dimethylformamide (31 ml) at 35° C., and then dimethylaminopyridine (19 mg) was added to the solution. The reaction liquid was adjusted to 30° C., subsequently diisopropylcarbodiimide (0.47 ml) was added thereto, and the mixture was stirred. After a lapse of 45 hours, diisopropylcarbodiimide (0.47 ml) was further added thereto, the temperature of the solution was raised to 35° C., and the mixture was stirred for 3 hours. After completion of the reaction, the reaction liquid was slowly added to a mixed solvent of ethyl acetate (31 ml) and diisopropyl ether (585 ml), and the mixture was stirred at room temperature. Subsequently, the mixture was left to stand until the intended product precipitated, and the supernatant was removed. Ethyl acetate/diisopropyl ether (1/19 (v/v); 308 ml) was further added to the precipitate thus obtained, and the mixture was stirred at room temperature. Subsequently, the supernatant was removed, the residue was dried under reduced, and thus, a crude product (1.15 g) was obtained. The crude product (1.15 g) thus obtained was dissolved in cold water (36 ml), and then centrifugal ultrafiltration was performed using a VIVASPIN TURBO 15 (MWCO: 10 kDa) (Sartorius AG) to remove low molecular weight compounds. The solution obtained after purification was freeze-dried, and thereby, the title compound (774 mg) was obtained. The drug content of the title compound thus obtained was 9.3% (mass fraction). Furthermore, the title compound was dissolved in water to a concentration of 5 mg/ml, and the particle size was measured. The particle size was 8.8 nm, and the compound formed micelles.

Reference Example 7 Block Copolymer Comprising Methoxy Polyethylene Glycol Moiety Having Molecular Weight of 2,000 and Moiety Having Structure in which Phenylalanine was Bonded to Side Chain of Polyaspartic Acid Having Polymerization Number of about 16

A methoxy polyethylene glycol-polyaspartic acid block copolymer (polymerization number of aspartic acid: about 16; 998 mg) produced by the method described in JP 3268913 B was dissolved in dimethylformamide (12 ml) at 35° C., and phenylalanine benzyl ester hydrochloride (1.27 g; 1.05 equivalents with respect to carboxyl groups), diisopropylethylamine (0.77 ml), and dimethylaminopyridine (51 mg) were added to the solution. The liquid temperature was cooled to 25° C., subsequently diisopropylcarbodiimide (1.27 ml) was added thereto, and the mixture was stirred at the same temperature. After a lapse of 21 hours, diisopropylcarbodiimide (0.64 ml) was further added thereto, and the mixture was stirred for 2 hours. After completion of the reaction, the mixture was slowly added to a mixed solvent of ethyl acetate (23 ml) and diisopropyl ether (207 ml), and the mixture was stirred at room temperature. Subsequently, the mixture was left to stand until the intended product precipitated, and the supernatant was removed. Ethyl acetate/diisopropyl ether (1/19 (v/v); 230 ml) was added to the precipitate thus obtained, and the precipitate was collected by filtration and then was dried under reduced pressure. Thus, a crude product (2.7 g) was obtained. The crude product (2.7 g) thus obtained was dissolved in a mixed liquid of acetonitrile (20 ml) and water (20 ml), and the solution was treated with an ion exchange resin (DOWEX 50 ($H^+$) manufactured by The Dow Chemical Company; 25 ml) for 5 hours under ice cooling. The ion exchange resin was filtered, and then the filtrate was concentrated under reduced pressure to remove acetonitrile. Next, the residue was freeze-dried, and thereby a benzyl-protected form of the title compound (1.94 g) was obtained. The benzyl-protected form (1.88 g) thus obtained was dissolved in N-methylpyrrolidone (34 ml) at 35° C. The reaction liquid was adjusted to 30° C., and then hydrous Pd/C (10%) (188 mg) was added thereto. The mixture was stirred for 25 hours at the same temperature in a hydrogen atmosphere. After completion of the reaction, the mixture was treated with activated carbon, and the filtrate was slowly added to diisopropyl ether (646 ml). The mixture was stirred at room temperature, subsequently the mixture was left to stand until the intended product precipitated, and the supernatant was removed. A mixed solvent of ethyl acetate and diisopropyl ether was added to the precipitate thus obtained, and the precipitate was dissolved in water and was freeze-dried. Thus, the title compound (1.5 g) was obtained.

Example 15 Production of Example 15 Compound (Conjugate of Block Copolymer Comprising Methoxy Polyethylene Glycol Moiety Having Molecular Weight of 2,000 and Moiety Having Structure in which Phenylalanine was Bonded to Side Chain of Polyaspartic Acid Having Polymerization Number of about 16, with trans,cis,cis-[PtCl(OH)(R,R-dach)(ox)]; in Formula (I), $R_1$=Me (Methyl Group), $R_2$=Trimethylene Group, $R_3$=Ac (Acetyl Group), $R_4$=Structure of (i) of Formula (II) (W=Residue Obtained by Eliminating H from Hydroxyl Group of Hexa-Coordinated Platinum Complex, or Isopropylaminocarbonylisopropylamino Group, T=Hydrogen Atom), $R_5$=Isopropylaminocarbonylisopropylamino Group, $d+e+f+g+h+i+j=16$, and $a=46$)

The block copolymer (0.8 g) produced in Reference Example 7, comprising a methoxy polyethylene glycol moiety and a moiety having a structure in which phenylalanine was bonded to a side chain of a polyaspartic acid having a polymerization number of about 16, was dissolved in dimethylformamide (40 ml) at 35° C. The reaction liquid was adjusted to 30° C., subsequently the hexa-coordinated platinum complex (532 mg) obtained in Reference Example 1, dimethylaminopyridine (24 mg), and diisopropylcarbodiimide (0.61 ml) were added to the reaction liquid, and the mixture was stirred. After a lapse of 45 hours, diisopropylcarbodiimide (0.61 ml) was further added thereto, the temperature of the solution was raised to 35° C., and the solution was stirred for 3 hours. After completion of the reaction, the reaction liquid was slowly added to a mixed solvent of ethyl acetate (40 ml) and diisopropyl ether (360 ml), and the mixture was stirred at room temperature. The mixture was left to stand until the intended product precipitated, and the supernatant was removed. Ethyl acetate/diisopropyl ether (1/9 (v/v); 400 ml) was further added to the precipitate thus obtained, and a crude product (1.2 g) was collected by filtration. The crude product (1.1 g) thus obtained was dissolved in a 5% aqueous solution of acetonitrile (60 ml), and then centrifugal ultrafiltration was performed using a VIVASPIN TURBO 15 (MWCO: 10 kDa) (Sartorius AG) to remove low molecular weight compounds. The solution obtained after purification was freeze-dried, and thereby the title compound (719 mg) was obtained. The drug content of the title compound was 13.3% (mass fraction). Furthermore, the title compound was dissolved in water to a concentration of 5 mg/ml, and the particle size was measured. The particle size was 32 nm, and the compound formed micelles.

Reference Example 8 Block Copolymer Comprising Methoxy Polyethylene Glycol Moiety Having Molecular Weight of 2,000 and Moiety Having Structure in which Phenylalanine was Bonded to Side Chain of Polyaspartic Acid Having Polymerization Number of about 12

The methoxy polyethylene glycol-polyaspartic acid block copolymer (polymerization number of aspartic acid: about 12; 1.54 g) produced by the method described in JP 3268913 B was dissolved in dimethylformamide (97 ml) at 35° C., and phenylalanine benzyl ester hydrochloride (1.04 g; 0.66 equivalents with respect to carboxyl groups), diisopropylethylamine (0.70 ml), dimethylaminopyridine (66 mg), and dimethylformamide (11 ml) were added to the solution. The liquid temperature was cooled to 25° C., and then diisopropylcarbodiimide (1.67 ml) was added thereto. The mixture was stirred for 22 hours at the same temperature, and then diisopropylcarbodiimide (0.23 ml) was added thereto. The temperature of the mixture was raised to 35° C., and the mixture was stirred for 3 hours. After completion of the reaction, the reaction mixture was slowly added to a mixed solvent of ethyl acetate (87 ml) and diisopropyl ether (1.65 l), and the mixture was stirred at room temperature. Subsequently, diisopropyl ether (200 ml) was added thereto, subsequently the mixture was left to stand until the intended product precipitated, and the supernatant was removed. The processes of adding ethyl acetate/diisopropyl ether (1/19 (v/v); 1.08 l) to the precipitate thus obtained and removing the supernatant were repeated two times, and the precipitate was collected by filtration and dried under reduced pressure. Thus, a crude product (2.5 g) was obtained. The crude product (2.5 g) thus obtained was dissolved in a mixed liquid of acetonitrile (50 ml) and water (50 ml), and an ion exchange resin (DOWEX 50 (H$^+$) manufactured by The Dow Chemical Company; 78 ml) was added to the solution. The mixture was stirred for one hour, the ion exchange resin was removed by filtration under reduced pressure, and then the filtrate was washed with a 50% aqueous solution of acetonitrile (30 ml). The filtrate was concentrated under reduced pressure to remove acetonitrile and then was freeze-dried. Thereby, a benzyl-protected form of the title compound (2.23 g) was obtained. The benzyl-protected form (2.19 g) thus obtained was dissolved in dimethylformamide (44 ml) at 35° C., and hydrous Pd/C (5%) (219 mg) was added thereto. The mixture was stirred at 30° C. for 25 hours in a hydrogen atmosphere. After completion of the reaction, the reaction mixture was treated with activated carbon and was filtered using Celite. The filtrate was slowly added dropwise to a mixed solvent of ethyl acetate (44 ml) and diisopropyl ether (836 ml), and the mixture was stirred at room temperature. Subsequently, the mixture was left to stand until the intended product precipitated, and the supernatant was removed. The processes of adding ethyl acetate/diisopropyl ether (1/19 (v/v); 440 ml) to the precipitate thus obtained and removing the supernatant were repeated two more times, and a precipitate was collected by filtration and dried under reduced pressure. Thus, the title compound (1.27 g) was obtained.

Example 16 Production of Example 16 Compound (Conjugate of Block Copolymer Comprising Methoxy Polyethylene Glycol Moiety Having Molecular Weight of 2,000 and Moiety Having Structure in which Phenylalanine was Bonded to Side Chain of Polyaspartic Acid Having Polymerization Number of about 12, with trans,cis,cis-[PtCl(OH)(R,R-dach)(ox)]; in Formula (I), $R_L$=Me (Methyl Group), $R_2$=Trimethylene Group, $R_3$=Ac (Acetyl Group), $R_4$=Structure of (i) of Formula (II) (W=Residue Obtained by Eliminating H from Hydroxyl Group of Hexa-Coordinated Platinum Complex, or Isopropylaminocarbonylisopropylamino Group, T=Hydrogen Atom), $R_5$=Isopropylaminocarbonylisopropylamino Group and Residue Obtained by Eliminating H from Hydroxyl Group of Hexa-Coordinated Platinum Complex, d+e+f+g+h+i+j=12, and a=46)

The block copolymer (1.27 g) produced in Reference Example 8, comprising a methoxy polyethylene glycol moiety and a moiety having a structure in which phenylalanine was bonded to a side chain of a polyaspartic acid having a polymerization number of about 12, was dissolved in dimethylformamide (29 ml) at 35° C., and then dimethylaminopyridine (27 mg), the hexa-coordinated platinum complex (986 mg) obtained in Reference Example 1, and dimethylformamide (44 ml) were added to the solution. The reaction liquid was adjusted to 30° C., and then diisopropylcarbodiimide (0.68 ml) was added thereto. After a lapse of 22 hours, diisopropylcarbodiimide (0.68 ml) was further added thereto, the temperature of the solution was raised to 35° C., and the solution was stirred for 3 hours. After completion of the reaction, the reaction liquid was slowly added to a mixed solvent of ethyl acetate (73 ml) and diisopropyl ether (1.39 l), and the mixture was stirred at room temperature. Subsequently, the mixture was left to stand until the intended product precipitated, and the supernatant was removed. Ethyl acetate/diisopropyl ether (1/19 (v/v); 731 ml) was added to the precipitate thus obtained and removing the supernatant were repeated another two times, and a crude product (2.23 g) was collected by filtration. The crude product (2.20 g) thus obtained was dissolved in cold water (80 ml), and then centrifugal ultrafiltration was performed using a VIVASPIN 20 (MWCO: 10 kDa) (Sartorius AG) to remove low molecular weight compounds. The solution obtained after purification was freeze-dried, and thereby the title compound (893 mg) was obtained. The drug content of the title compound thus obtained was 13.2% (mass fraction). Furthermore, the title compound was dissolved in water to a concentration of 5 mg/ml, and the particle size was measured. The particle size was 10 nm, and the compound formed micelles.

Reference Example 9 Block Copolymer Comprising Methoxy Polyethylene Glycol Moiety Having Molecular Weight of 2,000 and Moiety Having Structure in which Phenylalanine was Bonded to Side Chain of Polyaspartic Acid Having Polymerization Number of about 16

A methoxy polyethylene glycol-polyaspartic acid block copolymer (polymerization number of aspartic acid: about 16; 1.18 g) produced by the method described in JP 3268913 B was dissolved in dimethylformamide (24 ml) at 35° C., and phenylalanine benzyl ester hydrochloride (942 mg; 0.66 equivalents with respect to carboxyl groups) was added to the solution. The liquid temperature was cooled to 25° C., subsequently diisopropylethylamine (0.64 ml), dimethylaminopyridine (60 mg), and diisopropylcarbodiimide (1.51 ml) were added thereto, and the mixture was stirred at the same temperature. After a lapse of 21 hours, diisopropylcarbodiimide (0.61 ml) was further added to the mixture, the temperature of the solution was raised to 35° C., and the mixture was stirred for 4 hours. After completion of the reaction, the mixture was slowly added to a mixed solvent of ethyl acetate (12 ml) and diisopropyl ether (228 ml), and the mixture was stirred at room temperature. Subsequently, the mixture was left to stand until the intended product precipitated, and the supernatant was removed. The precipitate thus obtained was collected by filtration and was dried under reduced pressure, and a crude product (2.9 g) was obtained. The crude product (2.9 g) thus obtained was dissolved in a mixed liquid of acetonitrile (9 ml) and water (6 ml), and the solution was passed through a column packed with an ion exchange resin (DOWEX 50 ($H^+$) manufactured by The Dow Chemical Company; 40 ml) and was eluted with a 20% aqueous solution of acetonitrile (120 ml). The eluted fraction thus obtained was concentrated under reduced pressure to remove acetonitrile, and then the residue was freeze-dried. Thereby, a benzyl-protected form of the title compound (2.09 g) was obtained. The benzyl-protected form (2.0 g) thus obtained was dissolved in dimethylformamide (36 ml) at 30° C., and hydrous Pd/C (5%) (300 mg) was added to the solution. The mixture was stirred for 24 hours at the same temperature in a hydrogen atmosphere. After completion of the reaction, the reaction mixture was treated with activated carbon, and the filtrate was slowly added dropwise to a mixed solvent of ethyl acetate (36 ml) and diisopropyl ether (684 ml). The mixture was stirred at room temperature and then was left to stand until the intended product precipitated. The supernatant was removed. A mixed solvent of ethyl acetate and diisopropyl ether was added to the precipitate thus obtained, and the precipitate was collected by filtration and was dried under reduced pressure. Thus, the title compound (1.5 g) was obtained.

Example 17 Production of Example 17 Compound (Conjugate of Block Copolymer Comprising Methoxy Polyethylene Glycol Moiety Having Molecular Weight of 2,000 and Moiety Having Structure in which Phenylalanine was Bonded to Side Chain of Polyaspartic Acid Having Polymerization Number of about 16, with trans,cis,cis-[PtCl(OH)(R,R-dach)(ox)]; in Formula (I), $R_1$=Me (Methyl Group), $R_2$=Trimethylene Group, $R_3$=Ac (Acetyl Group), $R_4$=Structure of (i) of Formula (II) (W=Residue Obtained by Eliminating H from Hydroxyl Group of Hexa-Coordinated Platinum Complex, or Isopropylaminocarbonylisopropylamino Group, T=Hydrogen Atom), $R_5$=Isopropylaminocarbonylisopropylamino Group and Residue Obtained by Eliminating H from Hydroxyl Group of Hexa-Coordinated Platinum Complex, d+e+f+g+h+i+j=16, and a=46)

The block copolymer (0.9 g) produced in Reference Example 9, comprising a methoxy polyethylene glycol moiety and a moiety having a structure in which phenylalanine was bonded to a side chain of a polyaspartic acid having a polymerization number of about 16, was dissolved in dimethylformamide (34 ml) at 35° C. The reaction liquid was adjusted to 30° C., subsequently the hexa-coordinated platinum complex (765 mg) obtained in Reference Example 1, dimethylaminopyridine (21 mg), and diisopropylcarbodiimide (0.53 ml) were added, and the mixture was stirred. After a lapse of 45 hours, diisopropylcarbodiimide (0.61 ml) was further added to the mixture, the temperature of the solution was raised to 35° C., and the solution was stirred for 3 hours. After completion of the reaction, the reaction liquid was slowly added to a mixed solvent of ethyl acetate (34 ml) and diisopropyl ether (306 ml), and the mixture was stirred at room temperature. Subsequently, the mixture was left to stand until the intended product precipitated, and the supernatant was removed. Ethyl acetate/diisopropyl ether (1/9 (v/v); 390 ml) was further added to the precipitate thus obtained, and a crude product (1.61 g) was collected by filtration. The crude product (1.5 g) thus obtained was dissolved in a 5% aqueous solution of acetonitrile (60 ml), and then centrifugal ultrafiltration was performed using a VIVASPIN TURBO 15 (MWCO: 10 kDa) (Sartorius AG) to remove low molecular weight compounds. The solution obtained after purification was freeze-dried, and thereby, the title compound (882 mg) was obtained. The drug content of the title compound thus obtained was 15.2% (mass fraction). Furthermore, the title compound was dissolved in water to a concentration of 5 mg/ml, and the particle size was measured. The particle size was 11 nm, and the compound formed micelles.

Example 18 Production of Example 18 Compound
(Conjugate of Block Copolymer Comprising
Methoxy Polyethylene Glycol Moiety Having
Molecular Weight of 12,000 and Moiety Having
Structure in which Aspartic Acid-Alanine (4-Phenyl-1-Butanol) Ester was Bonded to Side Chain of
Polyaspartic Acid Having Polymerization Number
of about 43, with trans,cis,cis-[PtCl(OH)(R,R-dach)
(ox)]; in Formula (I), $R_1$=Me (Methyl Group),
$R_2$=Trimethylene Group, $R_3$=Ac (Acetyl Group),
$R_4$=Structure of (vii) of Formula (II) (W=Residue
Obtained by Eliminating H from Hydroxyl Group
of Hexa-Coordinated Platinum Complex, or Isopropylaminocarbonylisopropylamino Group;
T=Hydrogen Atom; and $R_8$=Residue Obtained by
Eliminating H from Amino Group of Alanine
(4-Phenyl-1-Butanol) Ester),
$R_5$=Isopropylaminocarbonylisopropylamino Group,
d+e+f+g+h+i+j=43, and a=273)

A block copolymer (364 mg) comprising a methoxy polyethylene glycol moiety and a moiety having a structure in which alanine (4-phenyl-1-butanol) ester was bonded to a side chain of a polyaspartic acid having a polymerization number of about 43, which had been produced by the method described in WO 2010/131675, and the hexa-coordinated platinum complex (135 mg) obtained in Reference Example 1 were dissolved in dimethylformamide (10 ml) at 35° C., and then dimethylaminopyridine (6 mg) was added thereto. The reaction liquid was adjusted to 25° C., and then diisopropylcarbodiimide (0.07 ml) was added thereto. After a lapse of 22 hours, diisopropylcarbodiimide (0.07 ml) was further added thereto, and the mixture was stirred for 4 hours. After completion of the reaction, the reaction liquid was slowly added to a mixed solvent of ethanol (20 ml), ethyl acetate (20 ml), and diisopropyl ether (160 ml), and the mixture was stirred at room temperature. Subsequently, the mixture was left to stand until the intended product precipitated, and the supernatant was removed. Ethanol/ethyl acetate/diisopropyl ether (1/1/8 (v/v/v); 100 ml) was further added to the precipitate thus obtained, and a crude product (441 mg) was collected by filtration. The crude product (420 mg) thus obtained was dissolved in a 30% aqueous solution of acetonitrile (30 ml), and then dialysis was performed using SPECTRA/POR 6 (MWCO: 3.5 kDa) (Spectrum, Inc.) to remove low molecular weight compounds. The solution obtained after purification was freeze-dried, and thereby, the title compound (399 mg) was obtained. The drug content of the title compound thus obtained was 21.9% (mass fraction). Furthermore, the title compound was dissolved in water to a concentration of 1 mg/ml, and the particle size was measured. The particle size was 75 nm, and the compound formed micelles.

Example 19 Production of Example 19 Compound
(Conjugate of Block Copolymer Comprising
Methoxy Polyethylene Glycol Moiety Having
Molecular Weight of 12,000 and Moiety Having
Structure in which Aspartic Acid-Glycine Ethyl
Ester was Bonded to Side Chain of Polyaspartic
Acid Having Polymerization Number of about 43,
with trans,cis,cis-[PtCl(OH)(R,R-dach)(ox)] and
Phenylalanine Benzyl Ester; in Formula (I), $R_1$=Me
(Methyl Group), $R_2$=Trimethylene Group, $R_3$=Ac
(Acetyl Group), $R_4$=Structure of (vii) of Formula
(II) (W=Residue Obtained by Eliminating H from
Hydroxyl Group of Hexa-Coordinated Platinum
Complex, Residue Obtained by Eliminating H from
Amino Group of Phenylalanine Benzyl Ester
(T=Hydrogen Atom), or Isopropylaminocarbonylisopropylamino Group; T=Hydrogen Atom; and
$R_e$=Residue Obtained by Eliminating H from
Amino Group of Glycine Ethyl Ester),
$R_5$=Isopropylaminocarbonylisopropylamino Group
and Residue Obtained by Eliminating H from
Amino Group of Phenylalanine Benzyl Ester
(T=Hydrogen Atom), d+e+f+g+h+i+j=43, and
a=273)

A block copolymer (510 mg) comprising a methoxy polyethylene glycol moiety and a moiety having a structure in which aspartic acid-glycine ethyl ester was bonded to a side chain of a polyaspartic acid having a polymerization number of about 43, which had been produced by the method described in WO 2010/131675, was dissolved in dimethylformamide (4.8 ml) at 35° C., and then the hexa-coordinated platinum complex (158 mg) obtained in Reference Example 1, dimethylaminopyridine (11 mg), and dimethylformamide (4.0 ml) were added to the solution. The reaction liquid was adjusted to 25° C., and diisopropylcarbodiimide (0.067 ml) was added thereto. After a lapse of 4 hours, phenylalanine benzyl ester hydrochloride (153 mg), diisopropylethylamine (0.089 ml), and diisopropylcarbodiimide (0.067 ml) were added thereto, and the mixture was stirred for another 20 hours. After completion of the reaction, the reaction liquid was slowly added to a mixed solvent of ethanol (13 ml) and diisopropyl ether (75 ml), and the mixture was stirred at room temperature. Subsequently, the mixture was left to stand until the intended product precipitated, and the supernatant was removed. Ethanol/diisopropyl ether (1/6 (v/v); 88 ml) was further added to the precipitate thus obtained, and a crude product (643 mg) was collected by filtration. The crude product (501 mg) thus obtained was dissolved in cold water (50 ml), and then dialysis was performed using SPECTRA/POR 6 (MWCO: 3.5 kDa) (Spectrum, Inc.) to remove low molecular weight compounds. The solution obtained after purification was freeze-dried, and thereby the title compound (440 mg) was obtained. The drug content of the title compound thus obtained was 18.1% (mass fraction). Furthermore, the title compound was dissolved in water to a concentration of 1 mg/ml, and the particle size was measured. The particle size was 33 nm, and the compound formed micelles.

Example 20 Production of Example 20 Compound (Conjugate of Block Copolymer Comprising Methoxy Polyethylene Glycol Moiety Having Molecular Weight of 2,000 and Polyaspartic Acid Moiety Having Polymerization Number of about 7, with trans,cis,cis-[PtCl(OH)(R,R-dach)(ox)] and Phenylalanine Benzyl Ester; in Formula (I), $R_1$=Me (Methyl Group), $R_2$=Trimethylene Group, $R_3$=Ac (Acetyl Group), $R_4$=Residue Obtained by Eliminating H from Hydroxyl Group of Hexa-Coordinated Platinum Complex, $R_5$=Isopropylaminocarbonylisopropylamino Group or Residue Obtained by Eliminating H from Amino Group of Phenylalanine Benzyl Ester (T=Hydrogen Atom), d+e+f+g+h+i+j=7, and a=46)

A block copolymer comprising a methoxy polyethylene glycol moiety having a molecular weight of 2,000 and a polyaspartic acid moiety having a polymerization number of about 7 (polymerization number of aspartic acid: about 7; 50 mg), which had been produced by the method described in JP 3268913 B, and the hexa-coordinated platinum complex (22.5 mg) obtained in Reference Example 1 were dissolved in dimethylformamide (2.15 ml) at 35° C., and then dimethylaminopyridine (1.53 mg) was added to the solution. The reaction liquid was adjusted to 25° C., and then diisopropylcarbodiimide (0.009 ml) was added thereto. After a lapse of 5 hours, phenylalanine benzyl ester hydrochloride (22 mg), diisopropylethylamine (0.013 ml), and diisopropylcarbodiimide (0.009 ml) were added thereto, and the mixture was stirred for another 21 hours. After completion of the reaction, the reaction liquid was slowly added to a mixed solvent of ethyl acetate (4.3 ml) and diisopropyl ether (48.7 ml), and the mixture was stirred at room temperature. Subsequently, the reaction mixture was left to stand until the intended product precipitated, and the supernatant was removed. The precipitate thus obtained was further washed with ethyl acetate/diisopropyl ether (1/9 (v/v); 20 ml), and the supernatant was removed. A crude product (79 mg) thus obtained was dissolved in cold water (12 ml), and then centrifugal ultrafiltration was performed using a VIVASPIN 6 (MWCO: 3 kDa) (Sartorius AG) to remove low molecular weight compounds. The solution obtained after purification was freeze-dried, and thereby the title compound (48.8 mg) was obtained. The drug content of the title compound thus obtained was 12.1% (mass fraction). Furthermore, the title compound was dissolved in water to a concentration of 5 mg/ml, and the particle size was measured. The particle size was 10.4 nm, and the compound formed micelles.

Reference Example 10 Synthesis of trans,cis,cis-[Pt(OH)(OAc)(R,R-dach)(ox)]

0.135 ml of 30% aqueous hydrogen peroxide was added to a liquid obtained by suspending l-OHP (200 mg) in 9 ml of acetic acid, and the mixture was stirred for 19 hours at room temperature in the dark. After completion of the reaction, the mixture was concentrated under reduced pressure several times while water was added to the system, and a solid was obtained. The solid thus obtained was recrystallized from ethanol/methanol, and thereby the title compound (55 mg) was obtained. H-NMR ($D_2O$): δ2.78-2.73 (2H, m), 2.17 (2H, d, J=9.2 Hz), 1.94 (3H, s), 1.54-1.44 (4H, m), 1.20-1.05 (2H, m), purity (HPLC, analysis conditions 1): 94.0%.

Reference Example 11 Synthesis of trans,cis,cis-[Pt(OCOCH($CH_2$Ph)N($CH_3$)—Boc)(Cl)(R,R-dach)(ox)]

The hexa-coordinated platinum complex (300 mg) obtained in Reference Example 1, N-α-Boc-N-α-methylphenylalanine (223.6 mg, Watanabe Chemical Industries, Ltd.), and HOBt.$H_2O$ (10.2 mg) were suspended in dimethylformamide (3 ml), and the suspension was cooled to 0° C. Subsequently, diisopropylcarbodiimide (0.155 ml) was added thereto, and the mixture was stirred for one hour. Subsequently, the mixture was returned to room temperature, and the mixture was allowed to react for another 6 hours. After completion of the reaction, ethyl acetate and water were added thereto, and the mixture was separated. An organic layer was washed with water and an aqueous solution of sodium hydrogen carbonate, and the organic layer was dried over sodium sulfate. Sodium sulfate was separated by filtration, and the filtrate was concentrated under reduced pressure. Diethyl ether was added to the residue thus obtained, and a solid was precipitated. The solid was collected by filtration, and thereby the title compound (178 mg) was obtained. LC/MS (analysis conditions 3); retention time 5.5 minutes, m/z 711 (M+1).

Reference Example 12 Synthesis of trans,cis,cis-[Pt(OCOCH($CH_2$Ph)NH($CH_3$))(Cl)(R,R-dach)(ox)] Trifluoroacetate The hexa-coordinated platinum complex (96 mg) obtained in Reference Example 11 was dissolved in dichloromethane (3 ml), the solution was cooled to 0° C., and then trifluoroacetic acid (1 ml) was added thereto. The mixture was stirred for 15 minutes at the same temperature, and the solvent was removed under reduced pressure. Diethyl ether was added to the residue thus obtained, a solid was precipitated, and the solid was collected by filtration. Thereby, the title compound (76 mg) was obtained. LC/MS (analysis conditions 4); retention time 4.1 minutes, m/z 611 (M+1).

Example 21 Production of Example 21 Compound (Conjugate of Block Copolymer Comprising Methoxy Polyethylene Glycol Moiety Having Molecular Weight of 2,000 and Moiety Having Structure in which N-Methylphenylalanine was Bonded to Side Chain of Polyaspartic Acid Having Polymerization Number of about 12, with trans,cis,cis-[PtCl(OH)(R,R-dach)(ox)]; in Formula (I), $R_1$=Me (Methyl Group), $R_2$=Trimethylene Group, $R_3$=Ac (Acetyl Group), $R_4$=Structure of (i) of Formula (II) (W=Residue Obtained by Eliminating H from Hydroxyl Group of Hexa-Coordinated Platinum Complex or Isopropylaminocarbonylisopropylamino Group, T=Methyl Group), $R_5$=Isopropylaminocarbonylisopropylamino Group, d+e+f+g+h+i+j=12, and a=46)

The title compound was obtained by a method similar to that of Example 12, using block copolymer comprising a methoxy polyethylene glycol moiety having molecular weight of 2,000—polyaspartic acid moiety (polymerization number of aspartic acid: about 12; 22 mg) produced by the method described in JP 3268913 B, the hexa-coordinated platinum complex (23 mg) obtained in Reference Example 12, HOBt.$H_2O$ (2.4 mg), diisopropylethylamine (0.016 ml), dimethylformamide (0.5 ml), and diisopropylcarbodiimide (0.048 ml). The drug content of the title compound thus obtained was 19.0% (mass fraction). Furthermore, the title compound was dissolved in water to a concentration of 1 mg/ml, and the particle size was measured. The particle size was 10.5 nm, and the compound formed micelles.

Comparative Example 1 Production of Comparative Example 1 Compound (Conjugate of Block Copolymer Comprising Methoxy Polyethylene Glycol Moiety Having Molecular Weight of 12,000 and Polyaspartic Acid Moiety Having Polymerization Number of about 43, with trans,cis,cis-[Pt(OH)(OAc)(R,R-dach)(ox)] and Phenylalanine Benzyl Ester; in Formula (I), $R_1$=Me (Methyl Group), $R_2$=Trimethylene Group, $R_3$=Ac (Acetyl Group), $R_4$=Residue Obtained by Eliminating H from Hydroxyl Group of Hexa-Coordinated Platinum Complex, $R_5$=Isopropylaminocarbonylisopropylamino Group or Residue Obtained by Eliminating H from Amino Group of Phenylalanine Benzyl Ester (T=Hydrogen Atom), d+e+f+g+h+i+j=43, and a=273)

The title compound was obtained by a method similar to that of Example 1, using trans,cis,cis-[Pt(OH)(OAc)(R,R-dach)(ox)], which was the hexa-coordinated platinum complex produced in Reference Example 10 having an acetoxy group and a hydroxyl group at the axial positions, was used instead of trans,cis,cis-[PtCl(OH)(R,R-dach)(ox)] of Example 1. The drug content of the title compound thus obtained was 20.2% (mass fraction). Furthermore, the title compound was dissolved in water to a concentration of 1 mg/ml, and the particle size was measured. The particle size was 15 nm, and the compound formed micelles.

Reference Example 13 Synthesis of trans,cis,cis-[Pt(OH)$_2$(R,R-dach)(ox)]

2.58 ml of 30% aqueous hydrogen peroxide was added to a liquid obtained by suspending l-OHP (900 mg) in 12 ml of distilled water, and the mixture was stirred for 20.5 hours at room temperature in the dark. After completion of the reaction, the reaction mixture was concentrated under reduced pressure several times while water was added to the system, and a solid was obtained. The solid thus obtained was recrystallized from distilled water, and the title compound (422 mg) was obtained. $^1$H-NMR (D$_2$O): δ2.74-2.72 (2H, m), 2.17 (2H, d, J=12.8 Hz), 1.54-1.45 (4H, m), 1.18-1.12 (2H, m), purity (HPLC, analysis conditions 1): >98.0%.

Comparative Example 2 Production of Comparative Example 2 Compound (Conjugate of Block Copolymer Comprising Methoxy Polyethylene Glycol Moiety Having Molecular Weight of 12,000 and Polyaspartic Acid Moiety Having Polymerization Number of about 43, with trans,cis,cis-[Pt(OH)$_2$(R,R-dach)(ox)] and Phenylalanine Benzyl Ester; in Formula (I), R: =Me (Methyl Group), $R_2$=Trimethylene Group, $R_3$=Ac (Acetyl Group), $R_4$=Residue Obtained by Eliminating H from Hydroxyl Group of Hexa-Coordinated Platinum Complex, $R_5$=Isopropylaminocarbonylisopropylamino Group or Residue Obtained by Eliminating H from Amino Group of Phenylalanine Benzyl Ester (T=Hydrogen Atom), d+e+f+g+h+i+j=43, and a=273)

The title compound was obtained by a method similar to that of Example 1, using trans,cis,cis-[Pt(OH)$_2$(R,R-dach)(ox)], which is a hexa-coordinated platinum complex produced in Reference Example 13, in which the ligands at the axial positions are both a hydroxyl group, instead of trans,cis,cis-[PtCl(OH)(R,R-dach)(ox)] of Example 1. The drug content of the title compound thus obtained was 12.5% (mass fraction). Furthermore, the title compound was dissolved in water to a concentration of 1 mg/ml, and the particle size was measured. The particle size was 44 nm, and the compound formed micelles.

Comparative Example 3 Production of Comparative Example 3 Compound (Polymer Conjugate in which Dachplatin (Pt(R,R-dach)Cl$_2$), which is Tetra-Coordinated Platinum Complex, is Coordination-Bonded to Block Copolymer Comprising Methoxy Polyethylene Glycol Moiety Having Molecular Weight of 12,000 and Polyglutamic Acid Moiety Having Polymerization Number of about 37)

A block copolymer (0.7 g) comprising a methoxy polyethylene glycol moiety having a molecular weight of 12,000 and a polyglutamic acid moiety having a polymerization number of about 37, which had been produced by the method described in JP 4745664 B, and phenylalanine benzyl ester hydrochloride (243 mg) were dissolved in dimethylformamide (18 ml) at 35° C. Subsequently, 4-(4,6-dimethoxy-1,3,5-triazin-2-yl)-4-methylmorpholinium chloride (260 mg) and diisopropylethylamine (0.15 ml) were sequentially added to the solution, and the mixture was stirred for 17 hours at the same temperature. After completion of the reaction, the reaction liquid was slowly added to a mixed solvent of ethanol (36 ml) and diisopropyl ether (144 ml), and the mixture was stirred at room temperature. Subsequently, the mixture was left to stand until the intended product precipitated, and the supernatant was removed. The precipitate thus obtained was collected by filtration and was dried under reduced pressure, and a crude product (0.8 g) of the polymer that served as a carrier was obtained. The crude product (0.8 g) thus obtained was dissolved in a 50% aqueous solution of acetonitrile (25 ml), and then the solution was passed through a column packed with an ion exchange resin (DOWEX 50 (H$^+$) manufactured by The Dow Chemical Company; 35 ml) and was eluted with a 50% aqueous solution of acetonitrile (17 ml) and a 50% aqueous solution of isopropyl alcohol. The eluted fraction thus obtained was concentrated under reduced pressure, and the organic solvent was removed. The residue was freeze-dried, and thereby, a polymer carrier (0.6 g) was obtained. The polymer carrier (0.5 g) thus obtained was dissolved in a 50% aqueous solution of isopropyl alcohol (22 ml), subsequently a 0.56 Normal aqueous solution of sodium hydroxide (0.9 ml) was added thereto, and the mixture was stirred for 1.5 hours at 40° C. Thereafter, an aqueous solution of [Pt(R,R-dach) (OH$_2$)$_2$] (NO$_3$)$_2$ (10.75 mM; 24 ml) prepared from K$_2$PtCl$_4$ by the method described in JP1989-313488 A was added thereto, and the mixture was stirred for 19.5 hours. After completion of the reaction, low molecular weight components were eliminated using a dialysis membrane (MWCO=14 kDa), subsequently maltose (2.0 g) was added to the dialyzed product, and the resulting mixture was freeze-dried. The drug content of the title compound thus obtained was 2.9% (mass fraction). Furthermore, the title compound was dissolved in water to a concentration of 1 mg/ml, and the particle size was measured. The particle size was 44 nm, and the compound formed micelles.

Test Example 1 Test on Platinum Complex Releasability of Example 1 Compound, Comparative Example 1 Compound, and Comparative Example 2 Compound Under Reducing Conditions Example 1 compound, Comparative Example 1 compound, and Comparative Example 2 compound were respectively dissolved in a 10 mM phosphate buffer solution containing ascorbic acid at a concentration of 600 μM, at a compound concentration of 1 mg/ml, and the solution was shaken at 37° C. in the dark. The solution was collected over time, and centrifugal ultrafiltration was performed using a VIVASPIN 500 (MWCO: 5 kDa) (Sartorius AG). The platinum content of the filtrate was quantitatively determined, and thereby the releasability of a platinum complex from a polymer conjugate was tested. For a comparison, in regard to the Example 1 compound, releasability in a case in which the compound was not dissolved in a 10 mM phosphate buffer solution without any added ascorbic acid, was also tested. Furthermore, the platinum content of the filtrate was quantitatively determined using ICP-OES, and the proportions of the amounts of released platinum with respect to the platinum content of the initial solution as 100% are presented in Table 1.

TABLE 1

| Compound name | $Y_1$ | Additive | 2 hr | 6 hr |
| --- | --- | --- | --- | --- |
| Example 1 compound | Cl | 600 μM Ascorbic acid | 76.4% | 80.1% |
| Comparative Example 1 compound | OAc | 600 μM Ascorbic acid | 1.6% | 2.3% |
| Comparative Example 2 compound | OH | 600 μM Ascorbic acid | 2.3% | 3.6% |
| Example 1 compound | Cl | — | 17.8% | 23.9% |

In regard to the Example 1 compound, release of 76.4% of the platinum complex bonded to the polymer was recognized after 2 hours from the initiation of the test under reducing conditions induced by addition of ascorbic acid. Meanwhile, in regard to the Comparative Example 1 compound and the Comparative Example 2 compound, release of the platinum complex bonded to the polymer was almost not recognized even after 6 hours from the initiation of the test, and it became clear that the platinum complex would not be released even under reducing conditions. Furthermore, in regard to the Example 1 compound, since the release ratio of the platinum complex after 2 hours from the initiation of the test without addition of ascorbic acid was 17.8%, and the release ratio under the conditions provided with addition of ascorbic acid as described above was 76.4%, it was confirmed that the release of the platinum complex was accelerated under reducing conditions. From the above, it was found that by selecting a hexa-coordinated platinum complex that is conjugated with a block copolymer comprising a polyethylene glycol structural moiety and a polyaspartic acid moiety or a polyglutamic acid moiety, a polymer conjugate of a hexa-coordinated platinum complex that releases the platinum complex under reducing conditions may be obtained.

Test Example 2 Test on Platinum Complex Releasability of Example 1 Compound and Comparative Example 3 Compound Under Reducing Conditions A release test was carried out in the same manner as in Test Example 1, for the Comparative Example 3 compound of a tetra-coordinated platinum complex having a bonding mode different from that of the Example 1 compound of a hexa-coordinated platinum complex. The results are presented in Table 2.

TABLE 2

| Compound name | $Y_1$ | Additive | 2 hr | 6 hr |
| --- | --- | --- | --- | --- |
| Example 1 compound | Cl | 600 μM Ascorbic acid | 76.4% | 80.1% |
| Example 1 compound | Cl | — | 17.8% | 23.9% |
| Comparative Example 3 compound | — | 600 μM Ascorbic acid | 1.4% | 2.7% |

TABLE 2-continued

| Compound name | $Y_1$ | Additive | 2 hr | 6 hr |
| --- | --- | --- | --- | --- |
| Comparative Example 3 compound | — | — | 1.5% | 1.6% |

In regard to the Comparative Example 3 compound, release of the platinum complex was almost not recognized even after 24 hours from the initiation of the test under reducing conditions provided by addition of ascorbic acid. The same test was also carried out under the conditions without addition of ascorbic acid; however, the release ratio was almost the same as the release ratio obtained under the conditions with addition of ascorbic acid, and any influence caused by addition of ascorbic acid was hardly seen. Therefore, it is obvious that in a case in which a tetra-coordinated platinum complex, which is used in Patent Document 1 and the like, is conjugated with a polymer by ligand exchange, the releasability is low.

Test Example 3 Antitumor Effect for Human Stomach Cancer 4-1ST Transplanted Mouse <Animal and Transplanted Tumor>

Human stomach cancer 4-1ST was subcultured subcutaneously in a BALB/cA-nu/nu mouse (hereinafter, nude mouse). Human stomach cancer 4-1ST was obtained from the Central Institute for Experimental Animals.

<Antitumor Test 1>

Human stomach cancer 4-1ST was collected subcutaneously from a nude mouse and was finely cut into blocks each measuring about 3 mm on each side. The tumor blocks thus obtained were subcutaneously transplanted into the dorsal side of nude mice using a trocar. On the 15$^{th}$ day after transplantation, where the average tumor volume had reached about 100 to 200 mm$^3$, various drugs were administered through the caudal vein. The use and dose (in terms of drug) of the various administered drugs are as follows. In regard to the Example 1 compound, the compound was dissolved in a 5% glucose injectable solution, and the solution was administered once at a dose of 25 mg/kg or 12.5 mg/kg. In regard to the Example 2 compound, the compound was dissolved in a 5% glucose injectable solution, and the solution was administered once at a dose of 25 mg/kg or 12.5 mg/kg. In regard to the Example 3 compound, the compound was dissolved in a 5% glucose injectable solution, and the solution was administered once at a dose of 20 mg/kg or 10 mg/kg. In regard to the Example 4 compound, the compound was dissolved in a 5% glucose injectable solution, and the solution was administered once at a dose of 20 mg/kg or 10 mg/kg. In regard to the Example 5 compound, the compound was dissolved in a 5% glucose injectable solution, and the solution was administered once at a dose of 20 mg/kg or 10 mg/kg. As a control drug, l-OHP was administered once at a dose of 20 mg/kg, and cisplatin was administered once at a dose of 10 mg/kg. Regarding the amounts of administration of l-OHP and cisplatin and the high amounts of administration of the various Example compounds, the maximum tolerable doses (MTD doses) were employed for all of the compounds. After the administration, the major axis (L) and the minor axis (W) of the tumor were measured over time using calipers, and the tumor volume (L×W×W×0.5) was calculated. The test was performed by employing four animals per group for all of a non-administered group as well as various drug-administered groups. During the period from the initiation of administration to the 21$^{st}$ day after administration, the relative tumor volume (T/C (%)) of each drug-administered group based on the relative tumor volume of a non-drug-administered group as 100 was calculated by the following formula as an index for the antitumor effect. The T/C (%) values of the various drug-administered groups are presented in Table 3.

T/C (%)=Relative tumor volume of administered group/relative tumor volume of non-administered group×100     Formula:

TABLE 3

| Compound | Amount of administration mg/kg | T/C (%) in various numbers of days after administration | | | | | | | |
|---|---|---|---|---|---|---|---|---|---|
| | | 0 | 3 | 5 | 7 | 10 | 14 | 17 | 21 |
| Non-administered group | 0 | 100 | 100 | 100 | 100 | 100 | 100 | 100 | 100 |
| Example 1 compound | 12.5 | 100 | 79 | 74 | 75 | 68 | 62 | 59 | 63 |
| | 25 | 100 | 54 | 38 | 24 | 21 | 19 | 23 | 22 |
| Example 2 compound | 12.5 | 100 | 72 | 65 | 64 | 77 | 72 | 72 | 71 |
| | 25 | 100 | 79 | 64 | 48 | 51 | 51 | 50 | 51 |
| Example 3 compound | 10 | 100 | 84 | 84 | 77 | 78 | 77 | 80 | 68 |
| | 20 | 100 | 59 | 40 | 33 | 31 | 30 | 26 | 25 |
| Example 4 compound | 10 | 100 | 68 | 60 | 61 | 59 | 41 | 42 | 46 |
| | 20 | 100 | 69 | 47 | 34 | 25 | 26 | 24 | 21 |
| Example 5 compound | 10 | 100 | 70 | 65 | 64 | 65 | 60 | 67 | 66 |
| | 20 | 100 | 57 | 34 | 22 | 19 | 18 | 22 | 19 |
| l-OHP | 20 | 100 | 72 | 57 | 49 | 49 | 45 | 46 | 41 |
| Cisplatin | 10 | 100 | 68 | 50 | 33 | 33 | 29 | 26 | 22 |

All of the Example compounds except for the Example 2 compound exhibited a superior antitumor effect compared to l-OHP. Particularly, in regard to the Example 4 compound, an antitumor effect to the same extent as that of l-OHP was maintained even at a low dose. The Example 2 compound exhibited an antitumor effect to the same extent as that of l-OHP. From the results described above, it is obvious that the present polymer conjugate of a hexa-coordinated platinum complex has an antitumor effect that is equal or superior to the antitumor effect of l-OHP.

<Antitumor Test 2>

Human stomach cancer 4-1ST was collected subcutaneously from a nude mouse and was cut into blocks each measuring about 3 mm on each side. The tumor blocks thus obtained were transplanted subcutaneously on the dorsal side of nude mice using a trocar. On the 17$^{th}$ day after transplantation, where the average tumor volume had reached about 100 to 200 mm$^3$, various drugs were administered through the caudal vein. The use and dose (in terms of drug) of the various administered drugs are as follows. In regard to the Example 11 compound, the compound was dissolved in a 5% glucose injectable solution, and the solution was administered once at a dose of 15 mg/kg or 7.5 mg/kg. In regard to the Example 12 compound, the compound was dissolved in a 5% glucose injectable solution, and the solution was administered once at a dose of 30 mg/kg or 15 mg/kg. As a control drug, l-OHP was administered once at a dose of 18 mg/kg, and cisplatin was administered once at a dose of 10 mg/kg. Regarding the amounts of administration of l-OHP and cisplatin and the high amounts of administration of the various Example compounds, the maximum tolerable doses (MTD doses) were employed for all of the compounds. After the administration, the major axis (L) and the minor axis (W) of the tumor were measured over time using calipers, and the tumor volume (L×W×W×0.5) was calculated. The test was performed by employing four animals per group for all of a non-administered group as well as various drug-administered groups. During the period from the initiation of administration to the 21$^{st}$ day after administration, the relative tumor volume (T/C (%)) of each drug-administered group based on the relative tumor volume of a non-drug-administered group as 100 was calculated by the following formula as an index for the antitumor effect. The T/C (%) values of the various drug-administered groups are presented in Table 4.

T/C (%)=Relative tumor volume of administered group/relative tumor volume of non-administered group×100       Formula:

After the administration, the body weights of the mice were measured over time. During the period from the initiation of administration to the 21$^{st}$ day after administration, the changes in the relative body weight based on the body weight on the day of initiation of administration as 1 are presented in Table 5.

TABLE 4

| Compound | Amount of administration mg/kg | T/C (%) in various numbers of days after administration | | | | | | |
|---|---|---|---|---|---|---|---|---|
| | | 0 | 4 | 7 | 11 | 14 | 18 | 21 |
| Non-administered group | | 100 | 100 | 100 | 100 | 100 | 100 | 100 |
| Example 11 compound | 7.5 | 100 | 80 | 67 | 61 | 58 | 52 | 55 |
| | 15 | 100 | 56 | 31 | 24 | 30 | 27 | 25 |
| Example 12 compound | 15 | 100 | 78 | 62 | 51 | 43 | 46 | 46 |
| | 30 | 100 | 55 | 35 | 26 | 24 | 21 | 20 |
| l-OHP | 18 | 100 | 84 | 52 | 50 | 50 | 60 | 57 |
| Cisplatin | 10 | 100 | 77 | 43 | 32 | 36 | 37 | 42 |

TABLE 5

| Compound | Amount of administration mg/kg | Relative body weight in numbers of days after administration | | | | | | |
|---|---|---|---|---|---|---|---|---|
| | | 0 | 4 | 7 | 11 | 14 | 18 | 21 |
| Non-administered group | | 1.00 | 0.99 | 0.97 | 0.96 | 1.00 | 1.03 | 1.00 |
| Example 11 compound | 7.5 | 1.00 | 0.91 | 0.96 | 0.95 | 0.99 | 0.99 | 0.99 |
| | 15 | 1.00 | 0.89 | 0.89 | 0.94 | 1.03 | 1.03 | 0.98 |
| Example 12 compound | 15 | 1.00 | 0.94 | 0.95 | 0.94 | 0.97 | 0.99 | 0.99 |
| | 30 | 1.00 | 0.92 | 0.93 | 0.95 | 1.03 | 1.01 | 0.98 |
| l-OHP | 18 | 1.00 | 0.78 | 0.83 | 0.93 | 1.03 | 1.09 | 1.05 |
| Cisplatin | 10 | 1.00 | 0.80 | 0.79 | 0.85 | 0.92 | 0.99 | 0.98 |

The Example 11 compound and the Example 12 compound exhibited a stronger antitumor effect than that of l-OHP and cisplatin. Meanwhile, weight reduction for the Example 11 compound and the Example 12 compound was low compared to l-OHP and cisplatin on the $4^{th}$ day of administration.

<Antitumor Test 3>

Human stomach cancer 4-1ST was collected subcutaneously from a nude mouse and was cut into blocks each measuring about 3 mm on each side. The tumor blocks thus obtained were transplanted subcutaneously on the dorsal side of nude mice using a trocar. On the $20^{th}$ day after transplantation, where the average tumor volume had reached about 100 to 200 mm$^3$, various drugs were administered through the caudal vein. The use and dose (in terms of drug) of the various administered drugs are as follows. In regard to the Example 7 compound, the compound was dissolved in a 5% glucose injectable solution, and the solution was administered once at a dose of 15 mg/kg or 7.5 mg/kg. In regard to the Example 16 compound, the compound was dissolved in a 5% glucose injectable solution, and the solution was administered once at a dose of 30 mg/kg or 15 mg/kg. As a control drug, l-OHP was administered once at a dose of 18 mg/kg or 9 mg/kg, and cisplatin was administered once at a dose of 10 mg/kg. Regarding the amounts of administration of l-OHP and cisplatin and the high amounts of administration of the various Example compounds, the maximum tolerable doses (MTD doses) were employed for all of the compounds. After the administration, the major axis (L) and the minor axis (W) of the tumor were measured over time using calipers, and the tumor volume (L×W×W×0.5) was calculated. The test was performed by employing four animals per group for all of a non-administered group as well as various drug-administered groups. During the period from the initiation of administration to the $21^{st}$ day after administration, the relative tumor volume (T/C (%)) of each drug-administered group based on the relative tumor volume of a non-drug-administered group as 100 was calculated by the following formula as an index for the antitumor effect. The T/C (%) values of the various drug-administered groups are presented in Table 6.

T/C (%)=Relative tumor volume of administered group/relative tumor volume of non-administered group×100   Formula:

After the administration, the body weights of the mice were measured over time. During the period from the initiation of administration to the $21^{st}$ day after administration, the changes in the relative body weight based on the body weight on the day of initiation of administration as 1 are presented in Table 7.

TABLE 6

| Compound | Amount of administration mg/kg | T/C (%) in various numbers of days after administration | | | | | | |
|---|---|---|---|---|---|---|---|---|
| | | 0 | 4 | 7 | 11 | 14 | 18 | 21 |
| Non-administered group | | 100 | 100 | 100 | 100 | 100 | 100 | 100 |
| Example 7 compound | 7.5 | 100 | 82 | 73 | 66 | 59 | 50 | 46 |
| | 15 | 100 | 49 | 30 | 27 | 30 | 31 | 29 |
| Example 16 compound | 15 | 100 | 73 | 73 | 53 | 60 | 56 | 51 |
| | 30 | 100 | 40 | 20 | 20 | 19 | 25 | 25 |
| l-OHP | 9 | 100 | 81 | 74 | 75 | 79 | 77 | 87 |
| | 18 | 100 | 60 | 37 | 36 | 47 | 50 | 52 |
| Cisplatin | 10 | 100 | 47 | 22 | 17 | 16 | 20 | 19 |

TABLE 7

| Compound | Amount of administration mg/kg | Relative body weight in numbers of days after administration | | | | | | |
|---|---|---|---|---|---|---|---|---|
| | | 0 | 4 | 7 | 11 | 14 | 18 | 21 |
| Non-administered group | | 1.00 | 0.99 | 1.01 | 1.01 | 1.01 | 1.00 | 1.01 |
| Example 7 compound | 7.5 | 1.00 | 0.97 | 1.01 | 1.01 | 1.02 | 1.01 | 1.02 |
| | 15 | 1.00 | 0.92 | 0.96 | 0.99 | 0.99 | 1.00 | 1.01 |

TABLE 7-continued

| Compound | Amount of administration mg/kg | Relative body weight in numbers of days after administration | | | | | | |
|---|---|---|---|---|---|---|---|---|
| | | 0 | 4 | 7 | 11 | 14 | 18 | 21 |
| Example 16 compound | 15 | 1.00 | 0.95 | 0.97 | 0.99 | 1.01 | 0.99 | 0.99 |
| | 30 | 1.00 | 0.94 | 0.99 | 1.00 | 1.01 | 1.00 | 1.00 |
| l-OHP | 9 | 1.00 | 0.96 | 1.00 | 1.01 | 1.02 | 1.02 | 1.02 |
| | 18 | 1.00 | 0.85 | 0.89 | 0.98 | 1.01 | 1.02 | 1.04 |
| Cisplatin | 10 | 1.00 | 0.91 | 0.95 | 0.99 | 1.01 | 0.97 | 1.01 |

The Example 7 compound and the Example 16 compound exhibited a stronger antitumor effect compared to l-OHP at the MTD doses. Meanwhile, weight reduction for the Example 7 compound and the Example 16 compound was low compared to l-OHP and cisplatin on the $4^{th}$ day of administration.

The invention claimed is:

1. A polymer conjugate of a hexa-coordinated platinum complex, the polymer conjugate comprising a block copolymer having a polyethylene glycol structural moiety and a polyaspartic acid moiety; and a hexa-coordinated platinum complex having a halogen atom and a hydroxyl group at the axial positions, the hexa-coordinated platinum complex being bonded directly to a side-chain carboxyl group of the block copolymer, wherein the polymer conjugate is represented by the following Formula (I):

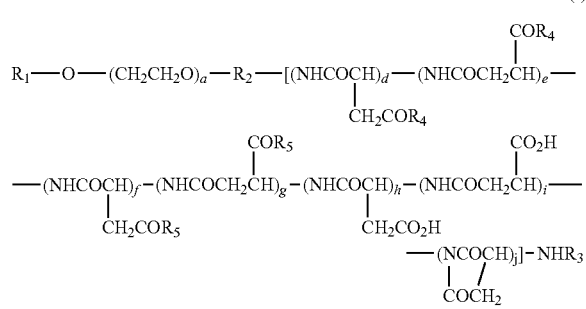

wherein $R_1$ represents a methyl group; $R_2$ represents a trimethylene group; $R_3$ represents an acetyl group; $R_4$ represents a residue of a hexa-coordinated platinum complex having a halogen atom and a hydroxyl group at the axial positions; $R_5$ represents a substituent selected from the group consisting of a residue obtained by eliminating H from an amino group of phenylalanine benzyl ester, and —$NR_9CONHR_{10}$; and $R_9$ and $R_{10}$ both represent a cyclohexyl group or an isopropyl group; a represents an integer from 5 to 11,500; d, e, f, g, h, i, and j each represents an integer from 0 to 200; d+e represents an integer from 1 to 200; d+e+f+g+h+i+j represents an integer from 2 to 200; and the bonding order of the various constituent units of the polyaspartic acid is arbitrary.

2. A polymer conjugate of a hexa-coordinated platinum complex, the polymer conjugate comprising a block copolymer having a polyethylene glycol structural moiety and a polyaspartic acid moiety; and a hexa-coordinated platinum complex having a halogen atom and a hydroxyl group at the axial positions, the hexa-coordinated platinum complex being bonded via a spacer to a side-chain carboxyl group of the block copolymer, wherein the polymer conjugate is represented by the following Formula (I):

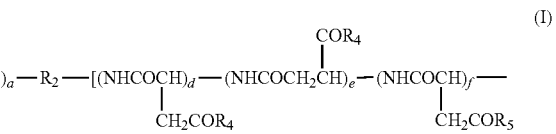

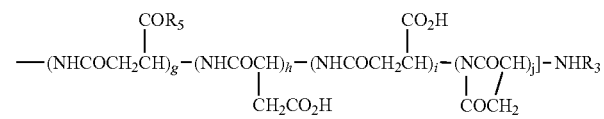

wherein $R_1$ represents a methyl group; $R_2$ represents a trimethylene group; $R_3$ represents an acetyl group; $R_4$ represents a substituent selected from the group represented by the following Formula (V):

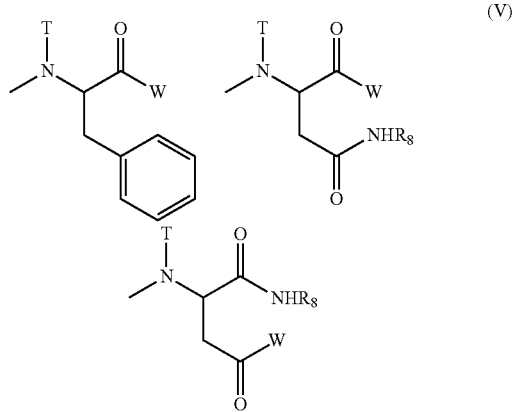

(V)

wherein W represents a substituent selected from the group consisting of a residue of a hexa-coordinated platinum complex having a halogen atom and a hydroxyl group at the axial positions, and —$NR_6CONHR_7$; $R_6$ and $R_7$ both represent a cyclohexyl group or an isopropyl group; T represents a hydrogen atom, a methyl group, an ethyl group, or a benzyl group; and $R_8$ represents a residue of an amino acid having the carboxylic acid protected, provided that at least one W among the substituents represents a residue of a hexa-coordinated platinum complex having a halogen atom and a hydroxyl group at the axial positions; $R_5$ represents —$NR_9CONHR_{10}$; and $R_9$ and $R_{10}$ both represent a cyclohexyl group or an isopropyl group; a represents an integer from 5 to 11,500; d, e, f, g, h, i, and j each represents an integer from 0 to 200; d+e represents an integer from 1 to 200; d+e+f+g+h+i+j represents an integer from 2 to 200; and the bonding order of the various constituent units of the polyaspartic acid is arbitrary.

3. The polymer conjugate of a hexa-coordinated platinum complex according to claim 2, wherein a represents an integer from 10 to 2,000; d, e, f, g, h, i, and j each represents an integer from 0 to 100; d+e represents an integer from 1 to 100; and d+e+f+g+h+i+j represents an integer from 4 to 100.

4. The polymer conjugate of a hexa-coordinated platinum complex according to claim 2, wherein the hexa-coordinated platinum complex having a halogen atom and a hydroxyl group at the axial positions is a hexa-coordinated platinum complex represented by the following Formula (XI):

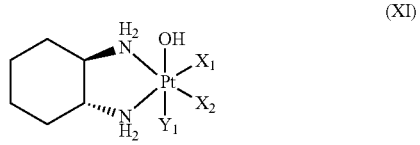

(XI)

wherein $X_1$ and $X_2$ both represent a halogen atom, or the two are linked together to form a dicarboxylate selected from the group consisting of oxalate, malonate, succinate, and o-phthalate; and $Y_1$ represents a halogen atom.

5. The polymer conjugate of a hexa-coordinated platinum complex according to claim 4, wherein $Y_1$ of the hexa-coordinated platinum complex represents a chlorine atom or a bromine atom; $X_1$ and $X_2$ both represent a chlorine atom or a bromine atom, or the two are linked together to form oxalate.

6. A medicine comprising the polymer conjugate of a hexa-coordinated platinum complex according to claim 2 as an active ingredient.

7. An antitumor agent comprising the polymer conjugate of a hexa-coordinated platinum complex according to claim 2 as an active ingredient.

8. The polymer conjugate of a hexa-coordinated platinum complex according to claim 1, wherein a represents an integer from 10 to 2,000; d, e, f, g, h, i, and j each represents an integer from 0 to 100; d+e represents an integer from 1 to 100; and d+e+f+g+h+i+j represents an integer from 4 to 100.

9. The polymer conjugate of a hexa-coordinated platinum complex according to claim 1, wherein the hexa-coordinated platinum complex having a halogen atom and a hydroxyl group at the axial positions is a hexa-coordinated platinum complex represented by the following Formula (XI):

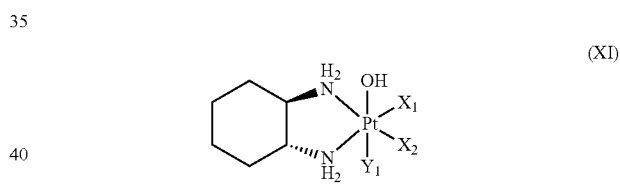

(XI)

wherein $X_1$ and $X_2$ both represent a halogen atom, or the two are linked together to form a dicarboxylate selected from the group consisting of oxalate, malonate, succinate, and o-phthalate; and $Y_1$ represents a halogen atom.

10. The polymer conjugate of a hexa-coordinated platinum complex according to claim 9, wherein $Y_1$ of the hexa-coordinated platinum complex represents a chlorine atom or a bromine atom; $X_1$ and $X_2$ both represent a chlorine atom or a bromine atom, or the two are linked together to form oxalate.

11. A medicine comprising the polymer conjugate of a hexa-coordinated platinum complex according to claim 1, as an active ingredient.

12. An antitumor agent comprising the polymer conjugate of a hexa-coordinated platinum complex according to claim 1 as an active ingredient.

* * * * *